United States Patent
Eldar-Finkelman

(10) Patent No.: US 7,446,092 B2
(45) Date of Patent: Nov. 4, 2008

(54) GLYCOGEN SYNTHASE KINASE-3 INHIBITORS

(75) Inventor: Hagit Eldar-Finkelman, Shoham (IL)

(73) Assignee: Tel Aviv University Future Technology Development L.P., Tel-Aviv (IL)

( * ) Notice: Subject to any disclaimer, the term of this patent is extended or adjusted under 35 U.S.C. 154(b) by 79 days.

(21) Appl. No.: 10/538,171

(22) PCT Filed: Dec. 11, 2003

(86) PCT No.: PCT/IL03/01057

§ 371 (c)(1),
(2), (4) Date: Dec. 8, 2005

(87) PCT Pub. No.: WO2004/052404

PCT Pub. Date: Jun. 24, 2004

(65) Prior Publication Data

US 2006/0135408 A1    Jun. 22, 2006

Related U.S. Application Data

(60) Provisional application No. 60/482,719, filed on Jun. 27, 2003, provisional application No. 60/432,644, filed on Dec. 12, 2002.

(51) Int. Cl.
*A61K 38/03*   (2006.01)
*A61K 38/10*   (2006.01)
*C07K 7/06*    (2006.01)
*C07K 7/08*    (2006.01)

(52) U.S. Cl. .......................... 514/7; 530/327; 530/328; 530/345

(58) Field of Classification Search ........................ None
See application file for complete search history.

(56) References Cited

U.S. PATENT DOCUMENTS

| | | | |
|---|---|---|---|
| 1,471,621 | A | 10/1923 | McCord |
| 2,046,068 | A | 6/1936 | Gray |
| 3,193,159 | A | 7/1965 | Swindler |
| 4,186,646 | A | 2/1980 | Martin |
| 5,462,101 | A | 10/1995 | Mouchmouchian |
| 6,057,117 | A | 5/2000 | Harrison et al. |
| 6,153,618 | A | 11/2000 | Schultz et al. |

FOREIGN PATENT DOCUMENTS

| | | |
|---|---|---|
| WO | WO 95/01376 | 1/1995 |
| WO | WO 97/33601 | 9/1997 |
| WO | WO 97/41854 | 11/1997 |
| WO | WO 98/16528 | 4/1998 |
| WO | WO 00/45237 | 3/2000 |
| WO | WO 00/59206 | 5/2000 |
| WO | WO 00/74663 | 12/2000 |
| WO | WO 01/49709 | 7/2001 |
| WO | WO 02/24941 | 3/2002 |
| WO | WO 2005/000192 | 6/2005 |

OTHER PUBLICATIONS

Taniguchi et al. Myristoylated Alanine-rich C Kinase Substrate . . . The Journal of Biological Chemistry. Jul. 15, 1994, vol. 269, No. 28, pp. 18299-18302.*
Manenti et al. Affinity Purificatiion and Characterization of Myristoylated . . . The Journal Of Biological Chemistry. Nov. 5, 1992, vol. 267, No. 31, pp. 22310-22315.*
Donella-Deana et al. "Dephosphorylation of Phosphopeptides by Colcineurin (Protein Phosphatase 2B)", Eur. J. Biochem., 219(1-2): 109-117, 1994. Tab.1,2.
Otaka et al. "Synthesis and Application of N-Box-L-2-Amino-4-(Diethylphosphono)-4-,4-Difluorobutanoic Acid for Solid-Phase Synthesis of Nonhydrolyzable Phosphoserine Peptide Analogues", Tetrahedron. Lett., 36(6): 927-930, 1995.
Othaka et al. "Development of New Methodology for the Synthesis of Functionalized α-Fluorophosphonates and Its Practical Application to the Preparation of Phosphopeptide Mimetics", Chem. Commun., 12: 1081-1082, 2000.
Pap et al. "Role of Glycogen Synthase Kinase-3 in the Phosphatidylinositol 3-Kinase/Akt Cell Survival Pathway", J. Biol. Chem., 273: 19929-19932, 1998.
Phiel "Molecular Targets of Lithium Action", Annu. Rev. Pharmacol. Toxicology, 41: 789-813, 2001.
Barrett et al. "Proteinase Inhibitors", Research Monographs in Cell and Tissue Physiology, V-XXII, 1986.
Roller et al. "Potent Inhibition of Protein-Tyrosine Phosphatase-1B Using the Phosphotyrosyl Mimetic Fluoro-O-Malonyl Tyrosine (FOMT)", Bioorg. Med. Chem. Lett., 8(16): 2149-2150, 1998.
Rubinfeld et al. "Binding of GSK3Beta to the APC-Beta-Catenin Complex and Regulation of Complex Assembly", Science, 272(5264): 1023-1026, 1996.
Sambrook et al. "Molecular Cloning: A Laboratory Manual", Cold Spring Harbour Press, 2nd Ed., V-XXXII, 1989.
Schiller et al. "Synthesis for Side-Chain Cyclized Peptide Analogs on Solid Supports", Int. J. Peptide Protein Res., 25: 171-177, 1985.
Shapiro et al. "Combined Fmoc-Alloc Strategy for A General SPPS of Phosphoserine Peptides: Preparation of Phosphorylation-Dependent Tau Antisera", Bioorg. Med. Chem., 5(1): 147-156, 1997.
Sherman et al. "Compatibility of Thioamides With Reverse Turn Features: Synthesis and Conformational Analysis of Two Model Cyclic Pseudopeptides Containing Thioamides as Backbone Modifications", Journal of the American Chemical Society, 112: 433-441, 1990.
Shulman et al. "Quantitation of Muscle Glycogen Synthesis in Normal Subjects and Subjects With Non-Insulin-Dependent Diabetes by 13C Nuclear Magnetic Resonance Spectroscopy", New England Journal of Medicine, 322(4): 223-228, 1990.

(Continued)

*Primary Examiner*—Jeffery E Russel

(57) ABSTRACT

Novel conjugates that are capable of inhibiting GSK-3 activity, a process of producing same, pharmaceutical compositions including same and methods of using same in the treatment of GSK-3 mediated conditions are disclosed. Methods of treating affective disorders using GSK-3 inhibitors are further disclosed.

9 Claims, 6 Drawing Sheets

OTHER PUBLICATIONS

Stambolic et al. "Lithium Inhibits Glycogen Synthase Kinase-3 Activity and Mimics Wingless Signalling in Intact Cells", Curr. Biol., 6: 1664-1668, 1996.

ter Haar et al. "Structure of GSK-3 Beta Reveals A Primed Phosphorylation Mechanism", Nat. Struct. Biol., 8(7): 593-596, 2001.

Thomas "Excitatory Amino Acids in Health and Disease", J. Am. Geriatr. Soc., 43: 1279-1289, 1995.

Thorsett et al. "Dipeptide Mimics. Conformationally Restricted Inhibitors of Angiotensin-Converting Enzyme", Biochem. Biophys. Res. Commun., 111(1): 166-171, 1983.

Tong et al. "Activation of Glycogen Synthase Kinase-3 Beta (GSK-3 Beta) by Platelet Activating Factor Mediates Migration and Cell Death in Cerebellar Granule Neurons", Eur. J. Neurosci., 13: 1913-1922, 2001.

Veber et al. "Conformationally Restricted Bicyclic Analogs of Somatostatin", Proc. Natl. Acad. Sci. USA, 75(6): 2636-2640, 1978.

Welsh et al. "Glycogen Synthase Kinase-3 Is Rapidly Inactivated in Response to Insulin and Phosphorylates Eukaryotic Initiation Factor Eif-2B", Biochem. J., 294(Pt 3): 625-629, 1993.

Wiemann et al. "Synthesis of Suitably Protected Hydroxymethylene Phosphonate- and 'Phosphat Phosphonate'-Analogues of Phosphoserine and Their Incorporation Into Synthetic Peptides", Tetrahedron, 56: 1331-1337, 2000.

Ye et al. "L-O-(2-Malonyl)Tyrosine: A New Phosphotyrosyl Mimetic for the Preparation of Src Homology 2 Domain Inhibitory Peptides", J. Med. Chem., 38(21): 4270-4275, 1995.

Eldar-Finkleman et al. "The Insulin Mimetic Action of Glycogen Synthase Kinase-3 Inhibitors", Diabetologia, 45(Suppl.2): A 70, 38th Annual Meeting for the European Association for the Study of Diabetes (EASD), Budapest, Hungary, 2002. Abstract.

Plotkin et al. "Insulin Mimetic Action of Synthetic Phosphorylated Peptide Inhibitors of Glycogen Synthase Kinase-3", Journal of Pharmacology and Experimental Therapeutics, 305(3): 974-980, 2003.

Leclerc et al. "Indirubins Inhibit Glycogen Synthase Kinase-3β and CDK5/P25, Two Proteins Kinases Involved in Abnormal Tau Phosphorylation in Alzheimer's Disease", The Journal of Biological Chemistry, 276(1): 251-260, 2001.

Hotamisligil et al. "IRS-1-Mediated Inhibition of Insulin Receptor Tyrosine Kinase Activity in TNT-α- and Obesity-Induced Insulin Resistance", Science, 271: 665-667, 1996.

Tanti et al. "Serine/Threonine Phosphorylation of Insulin Receptor Substrate 1 Modulates Insulin Receptor Signaling", The Journal of Biological Chemistry, 269(8): 6051-6057, 1994.

Fahraeus et al. "Inhibition of PRB Phosphorylation and Cell-Cycle Progression by A 20-Residue Peptide Derived From P16 CDKN2/INK4A", Current Biology, 6(1): 84-91, 1996.

Mitchell et al. "Heat-Stable Inhibitor Protein Derived Peptide Substrate Analogs: Phosphorylation by cAMP-Dependent and cGMP-Dependent Protein Kinases", Am. Chemical Soc., 1994.

Maniatis "Signal Transduction: Catalysis by A Multiprotein IkB Kinase Complex", Science, 278(5339): 818, 1997. Extract.

American Diabetes Association "Standards of Medical Care for Patients With Diabetes Mellitus", Diabetes Care, 17(6): 616-623, 1994.

Hawiger "Non-Invasive Intracellular Delivery of Functional Peptides", Curr. Opin. Chem. Biol., 3: 89-94, 1999.

Moreno et al. "Glycogen Synthase Kinase 3 Phosphorylation of Different Residues in the Presence of Different Factors: Analysis on TAU Protein", Mol.Cell.Biochem., 165(1):47-54, 1996. Tab.1.

Correll et al. "Inhibition of GSK3 Beta Mediates Cell Survival . . . Society For Neuroscience Abstracts" 25(2): 1519, 1999. Abstract No. 605.8.

Oelrichs et al. "Unique Toxic Peptides Isolated From Sawfly Larvae in Three Continents", Toxicon, 37(3): 537-544, 1999. Fig.3.

Fiol et al. "Ordered Multisite Protein Phosphorylation. Analysis of Glycogen Synthase. Kinase-3 Action Using Model Peptide Substrates", The Journal of Biological Chemistry, 265(11): 6061-6065, 1990. vol. 2: Abstract.

Barber et al. "Insulin Rescues Retinal Neurons From Apoptosis by A Phosphotidylinositol 3-Kinase/Akt-Mediated Mechanism That Reduces the Activation of Caspase-3", The Journal of Biological Chemistry, 276(350): 32814-32821, 2001.

Bijur et al. "Glycogen Synthase Kinese-3β Facilities Staurosporine- and Heat-Induced Apotosis", The Journal of Biological Chemistry, 275(11): 7583-7590, 2000.

Burke et al. "Potent Inhibition of Insulin Receptor Dephosphorylation by A Hexamer Peptide Containing the Phosphotyrosyl Mimetic F2Pmp", Biochemical and Biophysical Research Communications, 204(1): 129-134, 1994.

Burke et al. "4'-O[2(2-Fluoromalonyl)]-L-Tyrosine: A Phosphotyrosyl Mimic for the Preparation of Signal Transduction Inhabitory Peptides", J. Med. Chem., 39: 1021-1027, 1996.

Burke et al. "Small Molecule Interactions With Protein-Tyrosine Phosphatase PTP1B and Their Use in Inhibitor Design", Biochemistry, 35: 15989-15996, 1996.

Chen et al. "Why Is Phosphonodifluoromethyl Phenylalanine A More Potent Inhibitory Moiety Than Phosphonomethyl Phenylalanine Towards Protein-Tyrosine Phosphatases?", Biochemical and Biophysical Research Communications, 216(3): 976-984, (1995).

Cheng et al. "'Insulin-Like' Effects of Lithium Ion on Isolated Rat Adipocytes L. Stimulation of Glycogenesis Beyond Glucose Transport", Molecular and Cellular Biochemistry, 56: 177-182, 1983.

Chu et al. "Sequential Phosphorylation by Mitogen-Activated Protein Kinase and Glycogen Synthase Kinase 3 Represses Transcriptional Activation by Heat Shock Factor-1", The Journal of Biological Chemistry, 271(48): 30847-30857, 1996.

Cross et al. "Inhibition of Glycogen Synthase Kinase-3 by Insulin Mediated by Protein Kinase B", Nature, 78: 785-789, 1995.

Cross et al. "Selective Small-Molecule Inhibitors of Glycogen Synthase Kinase-3 Activity Protect Primary Neurons From Death", Journal of Neurochemistry, 77: 94-102, 2001.

Crowder et al. "Glycogen Synthase Kinase-3β Activity Is Critical for Neuronal Death Caused by Inhibiting Physpatidylinositol 3-Kinase or Akt But Not for Death Caused by Nerve Growth Factor Withdrawal", The Journal of the Biological Chemistry, 275(44): 34266-34271, 2000.

Dajani et al. "Crystal Structure of Glycogen Synthase Kinase 3β: Structural Basis for Phosphate-Primed Substrate Specificity and Autoinhibition", Cell, 105: 721-732, 2001.

Devlin et al. "Textbook of Biochemistry With Clinical Correlation", Wiley-Liss, 4th Ed., XVII-XXV, 1997.

Dugas et al. "Bioorganic Chemistry of the Amino Acids: Chemical Synthesis of Proteins", Springer Verlag, NY, p. 54-92, 1981.

Eldar-Finkelman et al. "Expression and Characterization of Glycogen Synthase Kinase-3 Mutants and Their Effect on Glycogen Synthase Activity in Intact Cells", Proc. Natl. Acad. Sci. USA, 93(19): 10228-10233, 1996.

Eldar-Finkelman et al. "Phosphorylation of Insulin Receptor Substrate 1 by Glycogen Synthase Kinase 3 Impairs Insulin Action", Proc. Natl. Acad. Sci. USA, 94(18): 9660-9664, 1997.

Eldar-Finkelman et al. "Increased Glycogen Synthase Kinase-3 Activity in Diabetes- and Obesity-Prone C57BL/6J Mice", Diabetes, 48(8): 1662-1666, 1999.

Fiol et al. "Formation of Protein Kinase Regognition Sites by Covalent Modification of Substrate. Molecular Mechanism for the Synergistic Action of Casein Kinase II and Glycogen Synthase Kinase 3", J. Biol. Chem., 262(29): 14042-14048, 1987.

Fiol et al. "Phosphoserine as A Recognition Determinant for Glycogen Synthase Kinase-3: Phosphorylation of A Synthetic Peptide Based on the G-Component of Protein Phosphatase-1", Arch. Biochem. Biophys., 267(2): 797-802, 1988.

Fiol et al. "A Secondary Phosphorylation of CREB341 at Ser129 Is Required for the cAMP-Mediated Control of Gene Expression. A Role for Glycogen Synthase Kinase-3 in the Control of Gene Expression", J. Biol. Chem., 269(51): 32187-32193, 1994.

Fu et al. "Design and Synthesis of A Pyrodone-Based Phosphtyrosine Mimetic", Bioorg. Med. Chem. Lett., 8(19): 2813-2816, 1998.

Gao et al. "Inhibition of Grb2 SH2 Domain Binding by Non-Phosphate-Containing Ligands. 2.4-(2-Malonyl)Phenylalanine as A Potent Phosphotyrosyl Mimetic", J. Med. Chem., 43(5): 911-920, 2000.

Gething et al. "Cell-Surface Expression of Influenza Haemagglutinin From A Cloned DNA Copy of the RNA Gene", Nature, 293(5834): 620-625, 1981.

Groves et al. "Structural Basis for Inhibition of the Protein Tyrosine Phosphatase 1B by Phosphotyrosine Peptide Mimetics", Biochemistry, 37(51): 17773-17783, 1998.

Hallstrom et al. "Regulation of Transcription Factor Pdrlp Function by An Hsp70 Protein in *Saccharomyces cerevisiae*", Mol. Cell Biol., 18(3): 1147-1155, 1998.

Hanger et al. "Glycogen Synthase Kinase-3 Induces Alzheimers Disease-Like Phosphorylation of Tau: Generation of Paired Helical Filament Epitopes and Neuronal Localisatoin of the Kinase", Neuroscience Letters, 147: 58-62, 1992.

Hawiger "Cellular Import of Functional Peptides to Block Intracellular Signaling", Curr. Opin. Immunol., 9(2): 189-194, 1997.

He et al. "Glycogen Synthase Kinase-3 and Dorsoventral Patterning in *Xenopus* Embryos", Nature, 374(6523): 617-622, 1995.

Higashimoto et al. "Human P53 Is Phosphorylated on Serines 6 and 9 in Response to DNA Damage-Inducing Agents", J. Biol. Chem., 275(30): 23199-23203, 2000.

Klein et al. "A Molecular Mechanism for the Effect of Lithium on Development", Natl. Acad. Sci. USA, 93: 8455-8459, 1996.

Kole et al. Protein-Tyrosine Phosphatase Inhibition by A Peptide Containing the Phosphotyrosyl Mimetic, L-O-Malonyltyrosine, Biochem. Biophys. Res. Commun., 209(3): 817-822, 1995.

Kole et al. "Specific Inhibition of Insulin Receptor Dephosphorylation by A Synthetic Dodecapeptide Containing Sulfotyrosyl Residues as Phosphotyrosyl Mimetic", Indian. J. Biochem. Biophys., 34(1-2): 50-55, 1997.

Latimer et al. "Stimulation of MAP Kinase by V-Raf Transformation of Fibroblasts Fails to Induce Hyperphosphorylation of Transfected Tau", FEBS Lett., 365: 42-46, 1995.

Lucas et al. "Decreased Nuclear Beta-Catenin, Tahyperphosphorylation and Neurodegeneration in GSK-3Beta Conditional Transgenic Mice", EMBO J., 20:27-39, 2001.

Lovestone et al. "Alzheimer's Disease-Like Phosphorylation of the Microtubule-Associated Protein Tau by Glycogen Synthase Kinase-3 in Transfected Mammalian Cells", Current Biology, 4: 1077-1086, 1995.

Mandelkow et al. "Tau as A Marker for Alzheimer's Disease", Trends Biochem. Sci., 18(12): 480-483, 1983.

Mandelkow et al. "Glycogen Synthase Kinase-3 and the Alzheimer-Like State of Micortubule-Associated Protein Tau", FEBS Letters, 314: 315-321, 1992.

Manji et al. "Lithium at 50: Have the Neuroprotective Effects of This Unique Cation Been Overlooked?", Biol. Psychiatry, 46(7): 929-940, 1999.

McKinsey et al. "Phosphorylation of the Pest Domain of IkappaB-beta Regulates the Function of NF-KappaB/IkappaBbeta Complexes", J. Biol. Chem., 272(36): 22377-22380, 1997.

Merrifield et al. "Solid Phase Peptide Synthesis I. The Synthesis of A Tetrapeptide", J. Am. Chem. Soc., 85: 2149-2154, 1963.

Mikol et al. "The Crystal Structures of the SH2 Domain of P56Ick Complexed With Two Phosphonopeptides Suggest A Gated Peptide Binding Site", J. Mol. Biol., 246(2): 344-355, 1995.

Morrison et al. "Organic Chemistry", Allyn and Bacon, 5th Ed., V-XXIV,1987.

Mulot et al. "PHF-Tau From Alzheimer's Brain Comprises Four Species on SDS-Page Which Can Be Mimicked by In Vitro Phosphorylation of Human Brain Tau by Glycogen Synthase Kinase-3 Beta", FEBS Lett., 349(3): 359-364, 1994.

Mulot et al. "Phosphorylation of Tau by Glycogen Synthase Kinase-3 Beta In Vitro Produces Species With Similar Electrophoretic and Immunogenic Properties to PHF-Tau From Alzheimer's Disease Brain", Biochem. Soc. Trans., 23(1): 45S, 1995.

Myers et al. "IRS-1 Activates Phosphatidylinositol 3'-Kinase by Associating With SRC Homology 2 Domains of P85D", Proc. Natl. Acad. Sci. USA, 89(21): 10350-10354, 1992.

Nicolaou et al. "Design and Synthesis of A Peptidomimeticemploying β-D-Glucose for Scaffolding", Peptides, ESCOM, 1990.

Nikoulina et al. "Regulation of Glycogen Synthase Activity in Cultured Skeletal Muscle Cells From Subjects With Type II Diabetes: Role of Chronic Hyperinsulinemia and Hyperglycemia", Diabetes, 46(6): 1017-1024, 1997.

Nikoulina et al. "Potential Role of Glycogen Synthase Kinase-3 in Skeletal Muscle Insulin Resitance of Type 2 Diabetes", Diabetes, 49(2): 263-271, 2000.

Nonaka et al. "Chronic Lithium Treatment Robustly Protects Neurons in the Central Nervous System Against Excitotoxicity by Inhibiting N-Methyl-D-Aspartate Rectpro-Mediated Calcium Influx", Proc. Natl. Acad. Sci. USA, 95: 2642-2647, 1998.

* cited by examiner

Figure 3a
Figure 3b
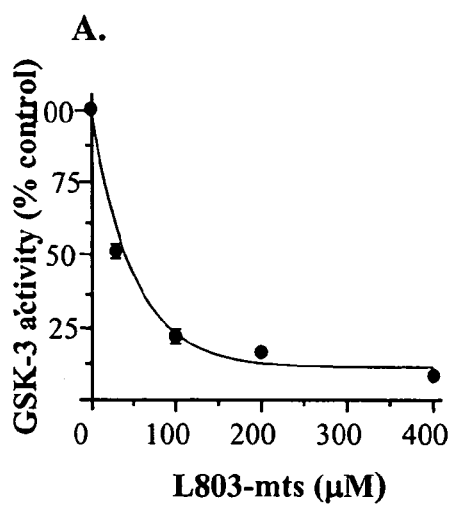
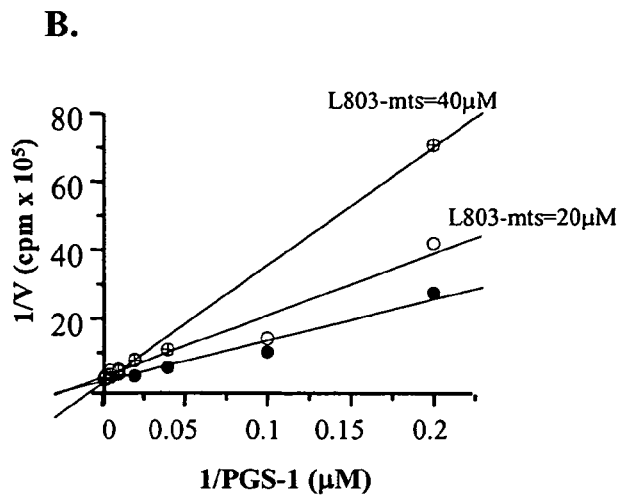
Figure 4
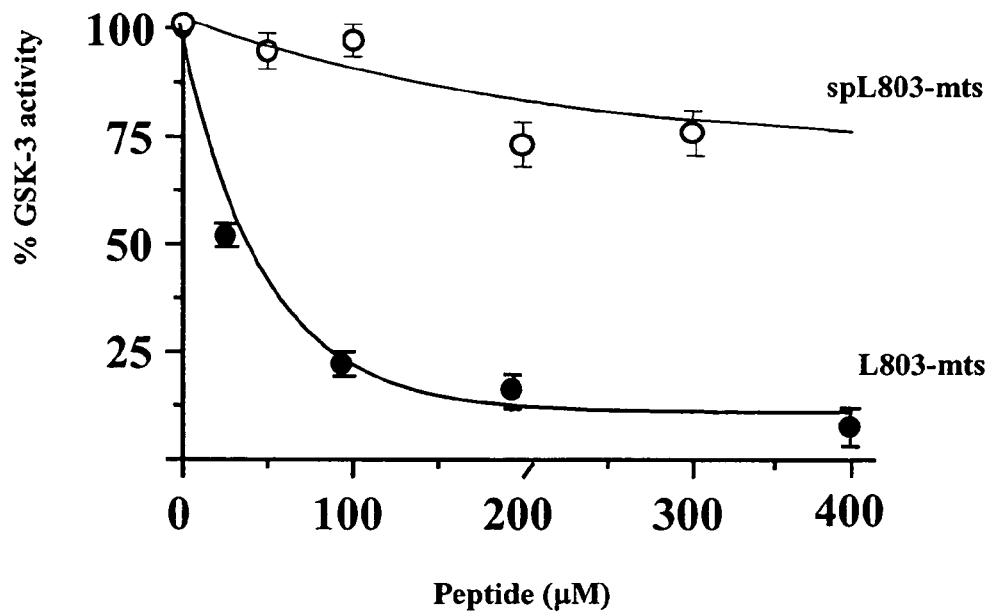

GLYCOGEN SYNTHASE KINASE-3 INHIBITORS

RELATED PATENT APPLICATION

This application is a National Phase Application of PCT/IL03/01057 having International Filing Date of 11 Dec. 2003, which claims the benefit of U.S. Provisional Patent Application No. 60/432,644 filed 12 Dec. 2002 and of U.S. Provisional Patent Application No. 60/482,719 filed 27 Jun. 2003.

FIELD AND BACKGROUND OF THE INVENTION

The present invention relates to novel conjugates for inhibiting glycogen synthase kinase-3 (GSK-3) and their use in regulating biological conditions mediated by GSK-3 activity and, more particularly, to the use of such conjugates in the treatment of biological conditions such as type II diabetes, neurodegenerative disorders and diseases and affective disorders. The present invention further relates to methods of treating affective disorders using GSK-3 inhibitors.

Protein kinases, the enzymes that phosphorylate protein substrates, are key players in the signaling of extracellular events to the cytoplasm and the nucleus, and take part in practically any event relating to the life and death of cells, including mitosis, differentiation and apoptosis. As such, protein kinases have long been favorable drug targets. However, since the activity of protein kinases is crucial to the well being of the cell, while their inhibition oftentimes leads to cell death, their use as drug targets is limited. Although cell death is a desirable effect for anticancer drugs, it is a major drawback for most other therapeutics.

Glycogen synthase kinase-3 (GSK-3), a member of the protein kinases family, is a cytoplasmic serine-threonine kinase that is involved in insulin signaling and metabolic regulation, as well as in Wnt signaling and the scheme of cell fate during embryonic development. Two similar isoforms of the enzyme, termed GSK-3α and GSK-3β, have been identified.

GSK-3 has long been considered as a favorable drug target among the protein kinase family since unlike other protein kinases, which are typically activated by signaling pathways, GSK-3 is normally activated in resting cells, and its activity is attenuated by the activation of certain signaling pathways such as those generated by the binding of insulin to its cell-surface receptor. Activation of the insulin receptor leads to the activation of protein kinase B (PKB, also called Akt), which in turn phosphorylates GSK-3, thereby inactivating it. The inhibition of GSK-3 presumably leads to the activation of glycogen synthesis. The intricate insulin-signaling pathway is further complicated by negative-feedback regulation of insulin signaling by GSK-3 itself, which phosphorylates insulin-receptor substrate-1 on serine residues (Eldar-Finkelman et al., 1997).

Therefore, synthetic GSK-3 inhibitors might mimic the action of certain hormones and growth factors, such as insulin, which use the GSK-3 pathway. In certain pathological situations, this scheme might permit the bypassing of a defective receptor, or another faulty component of the signaling machinery, such that the biological signal will take effect even when some upstream players of the signaling cascade are at fault, as in non-insulin-dependent type II diabetes.

The regulation of glycogen catabolism in cells is a critical biological function that involves a complex array of signaling elements, including the hormone insulin. Through a variety of mediators, insulin exerts its regulatory effect by increasing the synthesis of glycogen by glycogen synthase (GS). A key event in insulin action is the phosphorylation of insulin receptor substrates (IRS-1, IRS-2) on multiple-tyrosine residues, which results in simultaneous activation of several signaling components, including PI3 kinase (Myers et al, 1992)). Similarly, the activity of glycogen synthase is suppressed by its phosphorylation. There is a marked decrease in glycogen synthase activity and in glycogen levels in muscle of type II diabetes patients (Damsbo et al., 1991; Nikoulina et al., 1997; Shulman et al., 1990).

One of the earliest changes associated with the onset of type II (non-insulin dependent) diabetes is insulin resistance. Insulin resistance is characterized by hyperinsulemia and hyperglycemia. Although the precise molecular mechanism underlying insulin resistance is unknown, defects in downstream components of the insulin signaling pathway are considered to be the cause.

Glycogen synthase kinase-3 (GSK-3) is one of the downstream components of insulin signaling. It was found that high activity of GSK-3 impairs insulin action in intact cells, by phosphorylating the insulin receptor substrate-1 (IRS-1) serine residues (Eldar-Finkelman et al, 1997), and likewise, that increased GSK-3 activity expressed in cells results in suppression of glycogen synthase activity (Eldar-Finkelman et al, 1996). Further studies conducted in this respect uncovered that GSK-3 activity is significantly increased in epididymal fat tissue of diabetic mice (Eldar-Finkelman et al, 1999). Subsequently, increased GSK-3 activity was detected in skeletal muscle of type II diabetes patients (Nickoulina et al, 2000). Additional recent studies further established the role of GSK-3 in glycogen metabolism and insulin signaling (for review see, Eldar-Finkelman, 2002; Grimes and Jope, 2001; Woodgett, 2001), thereby suggesting that the inhibition of GSK-3 activity may represent a way to increase insulin activity in vivo.

GSK-3 is also considered to be an important player in the pathogenesis of Alzheimer's disease. GSK-3 was identified as one of the kinases that phosphorylate tau, a microtubule-associated protein, which is responsible for the formation of paired helical filaments (PHF), an early characteristic of Alzheimer's disease. Apparently, abnormal hyperphosphorylation of tau is the cause for destabilization of microtubules and PHF formation. Despite the fact that several protein kinases were shown to promote phosphorylation of tau, it was found that only GSK-3 phosphorylation directly affected tau ability to promote microtubule self-assembly (Hanger et al., 1992; Mandelkow et al., 1992; Mulot et al., 1994; Mulot et al., 1995). Further evidence for the GSK-3 role in this respect came from studies of cells overexpressing GSK-3 and from transgenic mice that specifically expressed GSK-3 in brain. In both cases GSK-3 led to generation of the PHF like epitope tau (Lucas et al., 2001).

GSK-3 is further linked with Alzheimer's disease by its role in cell apoptosis. The fact that insulin is a survival factor of neurons (Barber et al., 2001) and initiates its anti-apoptotic action through activation of PI3 kinase and PKB (Barber et al., 2001), suggested that GSK-3, which is negatively regulated by these signaling components, promotes neuronal apoptosis. Several studies have indeed confirmed this view, and showed that GSK-3 is critically important in life and death decision. Furthermore, its apoptotic function was shown to be independent of PI3 kinase. Overexpression of GSK-3 in PC12 cells caused apoptosis (Pap et al., 1998). Activation of GSK-3 in cerebellar granule neurons mediated migration and cell death (Tong et al., 2001). In human neuroblastoma SH-SY5Y cells, over expression of GSK-3 facilitated staurosporine-induced cell apoptosis (Bijur et al., 2000).

The relation between GSK-3 inhibition and the prevention of cells death has been further demonstrated by studies that showed that expression of Fratl, a GSK-3 β inhibitor, was sufficient to rescue neurons from death induced by inhibition of PI3 kinase (Crowder et al., 2000).

Another implication of GSK-3 was detected in the context of affective disorders, i.e., bipolar disorders and manic depression. This linkage was based on the findings that lithium, a primary mood stabilizer frequently used in bipolar disease, is a strong and specific inhibitor of GSK-3 at the therapeutic concentration range used in clinics (Klein et al., 1996; Stambolic et al., 1996; Phiel et al., 2001). This discovery has led to a series of studies that were undertaken to determine if lithium could mimic loss of GSK-3 activity in cellular processes. Indeed, lithium was shown to cause activation of glycogen synthesis (Cheng et al., 1983), stabilization and accumulation of β-catenin (Stambolic et al., 1996), induction of axis duplication in *Xenopus* embryo (Klein et al., 1996), and protection of neuronal death (Bijur et al., 2000). Valproic acid, another commonly used mood stabilizer has also been found to be an effective GSK-3 inhibitor (Chen et al., 1999). Altogether, these studies indicated that GSK-3 is a major in vivo target of lithium and valproic acid and thus has important implications in novel therapeutic treatment of affective disorders.

One mechanism by which lithium and other GSK-3 inhibitors may act to treat bipolar disorder is to increase the survival of neurons subjected to aberrantly high levels of excitation induced by the neurotransmitter, glutamate (Nonaka et al., 1998). Glutamate-induced neuronal excitotoxicity is also believed to be a major cause of neurodegeneration associated with acute damage, such as in cerebral ischemia, traumatic brain injury and bacterial infection. Furthermore, it is believed that excessive glutamate signaling is a factor in the chronic neuronal damage seen in diseases such as Alzheimer's, Huntington's, Parkinson's, AIDS associated dementia, amyotrophic lateral sclerosis (AML) and multiple sclerosis (MS) (Thomas, 1995).

Consequently, GSK-3 inhibitors are believed to be a useful treatment in these and other neurodegenerative disorders. Indeed, dysregulation of GSK-3 activity has been recently implicated in several CNS disorders and neurodegenerative diseases, including schizophrenia (Beasley et al., 2001; Kozlovsky et al., 2002), stroke, and Alzheimer's disease (AD) (Bhat and Budd, 2002; Hernandez et al., 2002; Lucas et al., 2001; Mandelkow et al., 1992).

Recent work has further demonstrated that GSK-3 is involved in additional cellular processes including development (He et al, 1995), oncogenesis (Rubinfeld et al, 1996) and protein synthesis (Welsh et al, 1993). Importantly, GSK-3 plays a negative role in these pathways. This further suggests that GSK-3 is a cellular inhibitor in signaling pathways.

In view of the wide implication of GSK-3 in various signaling pathways, development of specific inhibitors for GSK-3 will have important implications in various therapeutic interventions as well as in basic research.

As is mentioned above, some mood stabilizers were found to inhibit GSK-3. However, while the inhibition of GSK-3 both by lithium chloride (LiCl) (PCT International patent application WO 97/41854) and by purine inhibitors (PCT International patent application WO 98/16528) has been reported, these inhibitors are not specific for GSK-3. In fact, it was shown that these drugs affect multiple signaling pathways, and inhibit other cellular targets, such as inositol monophosphatase (IMpase) and histone deacetylases (Berridge et al., 1989; Phiel and Klein, 2001).

Similarly, an engineered cAMP response element binding protein (CREB), a known substrate of GSK-3, has been described (Fiol et al, 1994), along with other potential GSK-3 peptide inhibitors (Fiol et al, 1990). However, these substrates also only nominally inhibit GSK-3 activity.

Other GSK-3 inhibitors were recently reported. Two structurally related small molecules SB-216763 and SB-415286 (Glaxo SmithKline Pharmaceutical) that specifically inhibited GSK-3 were developed and were shown to modulate glycogen metabolism and gene transcription as well as to protect against neuronal death induced by reduction in PI3 kinase activity (Cross et al., 2001; Coghlan et al., 2000). Another study indicated that Induribin, the active ingredient of the traditional Chinese medicine for chronic myelocytic leukemia, is a GSK-3 inhibitor. However, Indirubin also inhibits cyclin-dependent protein kinase-2 (CDK-2) (Damiens et al., 2001). These GSK-3 inhibitors are ATP competitive and were identified by high throughput screening of chemical libraries. It is generally accepted that a major drawback of ATP-competitive inhibitors is their limited specificity (Davies et al., 2000).

There is thus a widely recognized need for, and it would be highly advantageous to have, small, highly-specific and highly-effective peptide inhibitors of GSK-3, devoid of the above limitations, which would be useful in treating conditions associated with GSK-3 activity such as diabetes type II, neurodegenerative disorders and affective disorders.

SUMMARY OF THE INVENTION

While conceiving the present invention, it was hypothesized that a conjugate of a polypeptide, preferably a short polypeptide, which is derived from a substrate of GSK-3 and a hydrophobic moiety would exert specific and effective inhibition of GSK-3, and would be further characterized by enhanced cell permeability.

While reducing the present invention to practice, as is detailed hereinbelow, it was indeed found that such conjugates specifically and effectively inhibit GSK-3 activity and a as result exert various therapeutic activities.

Thus, according to one aspect of the present invention there is provided a conjugate that is capable of inhibiting an activity of glycogen synthase kinase-3 (GSK-3), which comprises:

(a) a polypeptide having the amino acid sequence:

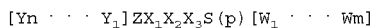

wherein, m equals 1 or 2; n is an integer from 1 to 50; S(p) is a phosphorylated serine residue or a phosphorylated threonine residue; Z is any amino acid residue excepting serine residue or threonine residue; and $X_1$, $X_2$, $X_3$, $Y_1$-Yn and $W_1$-Wm are each independently any amino acid residue; and According to further features in preferred embodiments of the invention described below, the at least one hydrophobic moiety is attached to an N-terminus and/or a C-terminus of the polypeptide, preferably to the N-terminus of the polypeptide.

According to still further features in the described preferred embodiments the at least one hydrophobic moiety comprises a hydrophobic peptide sequence, whereby the hydrophobic peptide sequence preferably comprises at least one amino acid residue selected from the group consisting of an alanine residue, a cysteine residue, a glycine residue, an isoleucine residue, a leucine residue, a valine residue, a phenylalanine residue, a tyrosine residue, a methionine residue, a proline residue and a tryptophan residue.

According to still further features in the described preferred embodiments the at least one hydrophobic moiety comprises a fatty acid, which is preferably attached to at least one amino acid residue.

According to still further features in the described preferred embodiments the fatty acid is selected from the group consisting of myristic acid, lauric acid, palmitic acid, stearic acid, oleic acid. linoleic acid and linolenic acid, preferably myristic acid.

According to still further features in the described preferred embodiments, $Y_3$ is any amino acid residue except a glutamic acid residue, Z is an alanine residue, and/or n is an integer from 1 to 15, preferably from 1 to 10.

In a preferred embodiment of the present invention, the conjugate has the amino acid sequence set forth in SEQ ID NO:16.

According to another aspect of the present invention there is provided a method of inhibiting an activity of GSK-3, which comprises contacting cells expressing GSK-3 with an effective amount of the conjugate described hereinabove.

The activity can be a phosphorylation activity and/or an autophosphorylation activity. Contacting the cells can be effected in vitro or in vivo.

According to further features in preferred embodiments of the invention described below, the method further comprises contacting the cells with at least one an additional active ingredient that is capable of altering an activity of GSK-3.

The additional active ingredient can be insulin or any active ingredient that is capable of inhibiting an activity of GSK-3, such as, but not limited to, lithium, valproic acid and a lithium ion.

Alternatively, the additional active indent can be an active ingredient that is capable of downregulating an expression of GSK-3, such as a polynucleotide, and more preferably a small interfering polynucleotide molecule directed to cause intracellular GSK-3 mRNA degradation.

The small interfering polynucleotide molecule can be selected from the group consisting of an RNAi molecule, an anti-sense molecule, a rybozyme molecule and a DNAzyme molecule.

According to yet another aspect of the present invention there is provided a method of potentiating insulin signaling, which comprises contacting insulin responsive cells, in vitro or in vivo, with an effective amount of the conjugate of the present invention, described hereinabove.

According to further features in preferred embodiments of the invention described below, the method further comprises contacting the cells contacting the cells with insulin.

According to still another aspect of the present invention there is provided a method of treating a biological condition associated with GSK-3 activity, which comprises administering to a subject in need thereof a therapeutically effective amount of the conjugate of the present invention.

According to further features in preferred embodiments of the invention described below, the biological condition is selected from the group consisting of obesity, non-insulin dependent diabetes mellitus, an insulin-dependent condition, an affective disorder, a neurodegenerative disease or disorder and a psychotic disease or disorder.

According to still further features in the described preferred embodiments the affective disorder is selected from the group consisting of a unipolar disorder (e.g., depression) and a bipolar disorder (e.g., manic depression).

According to still further features in the described preferred embodiments the neurodegenerative disorder results from an event selected from the group consisting of cerebral ischemia, stroke, traumatic brain injury and bacterial infection.

According to still further features in the described preferred embodiments the neurodegenerative disorder is a chronic neurodegenerative disorder, which preferably results from a disease selected from the group consisting of Alzheimer's disease, Huntington's disease, Parkinson's disease, AIDS associated dementia, amyotrophic lateral sclerosis (AML) and multiple sclerosis.

According to still further features in the described preferred embodiments the psychotic disorder is schizophrenia.

According to still further features in the described preferred embodiments the method according to this aspect of the present invention further comprises co-administering to the subject at least one additional active ingredient, which is capable of altering an activity of GSK-3, as is described hereinabove.

According to an additional aspect of the present invention there is provided a pharmaceutical composition that comprises, as an active ingredient, the conjugate of the present invention, and a pharmaceutically acceptable carrier. The pharmaceutical composition can further comprise at least one additional active ingredient, which is capable of altering an activity of GSK-3, as is described hereinabove.

In a preferred embodiment, the pharmaceutical composition is packaged in a packaging material and identified in print, on or in the packaging material, for use in the treatment of a biological condition associated with GSK-3 activity, as is detailed hereinabove.

The pharmaceutical composition of claim can be formulated in a delivery form selected from the group consisting of aerosol, aqueous solution, bolus, capsule, colloid, delayed release, depot, dissolvable powder, drops, emulsion, erodible implant, gel, gel capsule, granules, injectable solution, ingestible solution, inhalable solution, lotion, oil solution, pill, suppository, salve, suspension, sustained release, syrup, tablet, tincture, topical cream, transdermal delivery form.

According to yet an additional aspect of the present invention there is provided a process of producing the conjugate described hereinabove, which comprises providing the polypeptide described hereinabove; providing the at least one hydrophobic moiety described hereinabove; and conjugating the at least one hydrophobic moiety and the polypeptide.

The providing of the polypeptide can be by chemically synthesizing the polypeptide or by recombinantly producing the polypeptide.

According to still an additional aspect of the present invention there is provided a method of treating an affective disorder, which comprises administering to a subject in need thereof a therapeutically effective amount of at least one compound that is capable of specifically inhibiting an activity of GSK-3.

According to a further aspect of the present invention there is provided a method of up-regulating a β-catenin level in a hippocampus of a subject, which comprises administering to the subject an effective amount of at least one compound that is capable of specifically inhibiting an activity of GSK-3.

According to further features in preferred embodiments of the invention described below, the compound is a polypeptide having the amino acid sequence:

$$[Y_n \cdots Y_1] Z X_1 X_2 X_3 S(p) [W_1 \cdots W_m]$$

as is described hereinabove.

According to still further features in the described preferred embodiments the polypeptide has an amino acid sequence selected from the group consisting of the amino acid sequences set forth in SEQ ID NO:5, SEQ ID NO:6, SEQ ID NO:8, SEQ ID NO:9 and SEQ ID NO:12.

According to still further features in the described preferred embodiments the polypeptide further comprises at least one hydrophobic moiety, as is described hereinabove, being attached thereto.

According to still further features in the described preferred embodiments the compound has the amino acid sequence set forth in SEQ ID NO:16.

The present invention successfully addresses the shortcomings of the presently known configurations by providing novel conjugates that are capable of inhibiting GSK-3 activity in a highly specific and effective manner and can therefore be efficiently used in the treatment of a variety of biological conditions.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 3a-b present plots demonstrating the kinetic analysis of L803-mts, a representative example of a conjugate according to the present invention. FIG. 3a presents a plot demonstrating the GSK-3 inhibition activity of L803-mts. The ability of GSK-3 to phosphorylate PGS-1 peptide substrate was measured in the presence of indicated concentrations of L803-mts. The results represent the percentage of GSK-3 activity in control incubation in which peptide inhibitors were omitted. Results are mean of two independent experiments±SEM, where each point was assayed in triplicate. FIG. 3b presents a Lineweaver Burk plot presenting the inhibition of GSK-3 by L803-mts at indicated concentrations. The results represent phosphate incorporation into PGS-1 peptide substrate (CPM). Results show one representative experiment out of three. Each point is a mean of duplicated sample.

FIG. 4 presents comparative plots demonstrating the effect of L803-mts and cpL803-mts on GSK-3 activity in vitro. The ability of purified recombinant GSK-3β to phosphorylate PGS-1 peptide substrate was measured in the presence of indicated concentrations of L803-mts (filled circles) or the scrambled control peptide cpL803-mts (cp, open circles). The results represent the percentage of GSK-3 activity in the absence of the peptide inhibitors. Results are mean of three independent experiments±SEM, where each point was assayed in triplicate.

FIG. 5b presents the inhibition activity of purified GSK-3β by L803-mts, as compared with that of LE803-mts and LS803-mts (50 µM each).

DESCRIPTION OF THE PREFERRED EMBODIMENTS

Figure 1A:
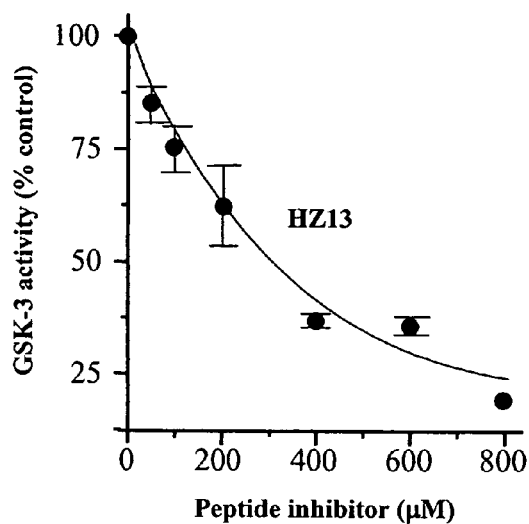
FIGS. 1a-b present plots demonstrating the GSK-3 inhibition activity of the phosphorylated peptide inhibitors HZ13 (FIG. 1a), pAHSF and L803 (FIG. 1b). The ability of GSK-3 to phosphorylate PGS-1 peptide substrate was measured in the presence of indicated concentrations of the peptide inhibitors. The results represent the percentage of GSK-3 activity in control incubation in which peptide inhibitors were omitted. Results are the mean of 3 independent experiments±SEM, where each point was assayed in triplicate.

The present invention is of novel conjugates, which are capable of inhibiting GSK-3 activity and can therefore be used in the treatment of biological conditions mediated by GSK-3. Specifically, the present invention is of (i) conjugates containing a polypeptide moiety and a hydrophobic moiety; (ii) a process of producing same; (iii) pharmaceutical compositions containing same; (iv) methods of using same for inhibiting GSK-3 activity, potentiating insulin signaling and up-regulating β-catenin levels in the hippocampus; and (v) methods of using same in the treatment of biological conditions such as, but not limited to, obesity, non-insulin dependent diabetes mellitus, insulin-dependent conditions, affective disorders, neurodegenerative diseases and disorders and psychotic diseases or disorders.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The present invention is based on the concept that relatively short peptides, derived from the recognition motif of GSK-3; may-serve as enzyme inhibitors. This concept, in turn, is based on the findings that GSK-3 has a unique recognition motif and therefore short peptides which are designed with reference to this motif are highly specific GSK-3 inhibitors, as is widely taught in WO 01/49709 and in U.S. Patent Application No. 20020147146A1, which are incorporated by reference as if fully set forth herein.

The unique recognition motif of GSK-3, set forth in SEQ ID NO:19, is $SX_1X_2X_3S(p)$, where S is serine or threonine, each of $X_1$, $X_2$ and $X_3$ is any amino acid, and S(p) is phosphorylated serine or phosphorylated threonine. Based on this recognition motif, a set of peptides, which differ one from another in various parameters (e.g., length, phosphorylation, sequence, etc.) have been designed, synthesized and were tested for their activity as either substrates or inhibitors of GSK-3 (see, for example, Table 3 and the accompanying description in the Examples section that follows).

Based on these experiments, a number of features, which would render a peptide an efficient GSK-3 inhibitor, have been determined. For example, it was found that the phosphorylated serine or threonine residue in the motif is necessary for binding Without this residue, the peptide will neither be a substrate nor an inhibitor. It was further determined that a serine (or threonine) residue upstream of the phosphorylated serine (or threonine) residue separated by three additional residues renders the peptide a GSK-3 substrate, whereas replacement of this serine or threonine residue by any other amino acid, preferably alanine, converts the substrate to a GSK-3 inhibitor. The nature of the three amino acids (denoted as $X_1X_2X_3$ in the sequence above) was also found to affect the inhibition activity of the peptide, as is detailed hereinafter in the Examples section. In one particular, in was found that the presence of glutamic acid as the $Y_3$ residue, which is detected in many GSK-3 substrates, reduces the inhibition activity of the peptide and therefore it is preferable to have any amino acid other than glutamic acid at the $Y_3$ position. It was further found that the number of the additional residues, outside the recognition motif, affect the inhibition potency of the peptide, such that, for example, a total number of between 7 and 50, preferably, between 7 and 20, more preferably between 10 and 13 amino acid residues, is preferable.

Hence, as is further described and exemplified in the Examples section that follows, it was found that polypeptides having the amino acid sequence:

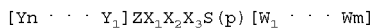

wherein m equals 1 or 2; n is an integer from 1 to 50; S(p) is a phosphorylated serine residue or a phosphorylated threonine residue; Z is any amino acid residue excepting serine residue or threonine residue; and $X_1$, $X_2$, $X_3$, $Y_1$-Yn and $W_1$-Wm are each independently any amino acid residue, are highly efficient and specific inhibitors of GSK-3.

It was further found that preferred polypeptides are those having an alanine residue at the Z position, having any amino acid residue excepting glutamic acid as $X_3$, and/or having between 7 and 20 amino acid residues, preferably between 10 and 13 amino acid residues and more preferably between 10 and 11 amino acid residues, such that n equals 1-15, preferably 1-10.

The efficacy and specificity of these polypeptide inhibitors have been successfully demonstrated so far in in vitro tests. However, while aiming at evaluating the efficacy of these inhibitors in in vivo tests, it was hypothesized by the present inventor that attaching to the polypeptides described above a hydrophobic moiety would enhance their membrane permeability. While reducing this hypothesis to practice, it was surprisingly found, in both in vitro and in vivo tests, that a conjugate of the polypeptide inhibitor described above and a fatty acid, as a hydrophobic moiety, attached at the N-terminus of the polypeptide, exerts higher inhibition of GSK-3 activity than a corresponding polypeptide devoid of a hydrophobic moiety.

Hence, according to one aspect of the present invention, there is provided a conjugate of the polypeptide described hereinabove and a hydrophobic moiety, which is capable of inhibiting an activity of GSK-3.

More specifically, the conjugate of the present invention comprises:

(a) a polypeptide having an amino acid sequence:

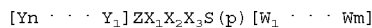

wherein m equals 1 or 2; n is an integer from 1 to 50; S(p) is a phosphorylated serine residue or a phosphorylated threonine residue; Z is any amino acid residue excepting serine residue or threonine residue; and $X_1$, $X_2$, $X_3$, $Y_1$-Yn and $W_1$-Wm are each independently any amino acid residue; and (b) one or more hydrophobic moieties that are attached to the polypeptide.

As used herein, the term "polypeptide" refers to an amino acid sequence of any length including full-length proteins or portions thereof, wherein the amino acid residues are linked by covalent peptide bonds. Preferably, the polypeptides of the present invention are relatively short polypeptides, having between 7 and 50 amino acid residues, preferably between 7 and 20 amino acid residues, more preferably between 10 and 13 amino acid residues, and are therefore referred to herein interchangeably as "peptides".

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N-terminus modification, C-terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Preferably, the peptides of the present invention are synthetically synthesized peptides.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom.

These modifications can occur at any of the bonds along the peptide chain and even at several (2-3) at the same time.

As used herein, the phrase "amino acid residue", which is also referred to herein, interchangeably, as "amino acid", describes an amino acid unit within a polypeptide chain. The amino acid residues within the polypeptides of the present invention can be either natural or modified amino acid residues, as these phrases are defined hereinafter.

As used herein, the phrase "natural amino acid residue" describes an amino acid residue, as this term is defined hereinabove, which includes one of the twenty amino acids found in nature.

As used herein, the phrase "modified amino acid residue" describes an amino acid residue, as this term is defined hereinabove, which includes a natural amino acid that was subjected to a modification at its side chain. Such modifications are well known in the art and include, for example, incorporation of a functionality group such as, but not limited to, a hydroxy group, an amino group, a carboxy group and a phosphate group within the side chain. This phrase therefore includes, unless otherwise specifically indicated, chemically modified amino acids, including amino acid analogs (such as penicillamine, 3-mercapto-D-valine), naturally-occurring non-proteogenic amino acids (such as norleucine), and chemically-synthesized compounds that have properties known in the art to be characteristic of an amino acid. The term "proteogenic" indicates that the amino acid can be incorporated into a protein in a cell through well-known metabolic pathways.

Accordingly, as used herein, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids which are linked via a peptide bond or a peptide bond analog to at least one addition amino acid as this term is defined herein.

Tables 1-2 below list all the naturally occurring amino acids (Table 1) and non-conventional or modified amino acids (Table 2).

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Ile | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-α-methylalnine | Dnmala |
| D-α-methylarginine | Dnmarg |
| D-α-methylasparagine | Dnmasn |
| D-α-methylasparatate | Dnmasp |
| D-α-methylcysteine | Dnmcys |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylamihoisobutyrate | Nmaib |
| N-(1-methylpropyl)glycine | Nile |
| N-(2-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |

TABLE 2-continued

| Non-conventional amino acid | Code |
|---|---|
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | mser |
| L-α-methylvaline | Mtrp |
| L-α-methylleucine | Mval |
| N-(N-(2,2-diphenylethyl) | Nnbhm |
| carbamylmethyl-glycine | Nnbhm |
| 1-carboxy-1-(2,2-diphenylethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgin |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcyclopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cyclododeclglycine | Ncdod |

TABLE 2-continued

| Non-conventional amino acid | Code |
|---|---|
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-indolylethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylserine | Dnmser |
| D-N-methylthreonine | Dnmthr |
| N-(1-methylethyl)glycine | Nva |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| N-(3-guanidinopropyl)glycine | Narg |
| N-(1-hydroxyethyl)glycine | Nthr |
| N-(hydroxyethyl)glycine | Nser |
| N-(imidazolylethyl)glycine | Nhis |
| N-(3-indolylethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl)carbamylmethyl(1)glycine | Nnbhe |

The peptides of the present invention are preferably utilized in a linear form, although it will be appreciated that in cases where cyclization does not severely interfere with peptide characteristics, cyclic forms of the peptide can also be utilized).

Cyclic peptides can either be synthesized in a cyclic form or configured so as to assume a cyclic form under desired conditions (e.g., physiological conditions).

For example, a peptide according to the teachings of the present invention can include at least two cysteine residues flanking the core peptide sequence. In this case, cyclization can be generated via formation of S—S bonds between the two Cys residues. Side-chain to side chain cyclization can also be generated via formation of an interaction bond of the formula —(—CH$_2$—)n-S—CH$_2$—C—, wherein n=1 or 2, which is possible, for example, through incorporation of Cys or homoCys and reaction of its free SH group with, e.g., bromoacetylated Lys, Orn, Dab or Dap. Furthermore, cyclization can be obtained, for example, through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N((CH$_2$)n-COOH)—C(R)H—COOH or H—N ((CH$_2$)n-COOH)—C(R)H—NH$_2$, wherein n=1-4, and further wherein R is any natural or non-natural side chain of an amino acid.

The peptides of the present invention are preferably peptidomimetics, as this term is define hereinabove, which mimic the structural features of the critical amino acid motif ZX$_1$X$_2$X$_3$S(p).

Protein phosphorylation plays a crucial part in the biochemical control of cellular activity. Phosphorylation usually means formation of a phosphate ester bond between a phosphate (PO$_4$) group and an amino acid containing a hydroxyl (OH) group (tyrosine, serine and threonine). Many phosphorylation sites in proteins act as recognition elements for binding to other proteins, and those binding events activate or deactivate signaling and other pathways. Protein phosphorylation thus acts as a switch to turn biochemical signaling on and off.

Phosphopeptide mimetics are a subclass of peptidomimetics that contain analogs of phosphorylated tyrosine, serine and threonine. Phosphate esters may be hydrolyzed by various enzymes, thus turning off a phosphorylation signal. Phosphopeptide mimetics, however, usually contain non-hydrolyzable analogs to prevent inactivation (Burke et al, 1994a; Burke et al, 1996a; Chen et al, 1995; Wiemann et al, 2000; Shapiro et al, 1997; Otaka et al, 1995; Otaka et al, 2000). General examples of phosphopeptide mimetics in the art include SH2 domain analogs (Burke et al, 1994a; Fu et al, 1998; Gao et al, 2000; Mikol et al, 1995; Ye et al, 1995), transcription factor NF-(kappa)B analog (McKinsey et al, 1997), P53 analog (Higashimoto et al, 2000) and protein-tyrosine phosphatase inhibitors (Burke et al, 1994b; Burke et al, 1996b; Groves et al, 1998; Kole et al, 1995; Kole et al, 1997; Roller et al, 1998).

Commercially available software packages can be used to design small peptides and/or peptidomimetics containing, phosphoserine or phosphothreonine analogs, preferably non-hydrolyzable analogs, as specific antagonists/inhibitors. Suitable commercially available software for analyzing crystal structure, designing and optimizing small peptides and peptidomimetics include, but are not limited to: Macromolecular X-ray Crystallography QUANTA Environment (Molecular Simulations, Inc.); TeXsan, BioteX, and SQUASH (Molecular Structure Corporation); and Crystallographica (Oxford Cryostsystems).

The peptides according to the present invention can further include salts and chemical derivatives of the peptides. As used herein, the phrase "chemical derivative" describes a polypeptide of the invention having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. Also included as chemical derivatives are those peptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. The chemical derivatization does not comprehend changes in functional groups which change one amino acid to another.

As is mentioned hereinabove, some useful modifications are designed to increase the stability of the peptide in solution and, therefore, serve to prolong the half-life of the peptide in solutions, particularly biological fluids, such as blood, plasma or serum, by blocking proteolytic activity in the blood. Hence, the peptides of the present invention can have a stabilizing group at one or both termini. Typical stabilizing groups include amido, acetyl, benzyl, phenyl, tosyl, alkoxycarbonyl, alkyl carbonyl, benzyloxycarbonyl and the like end group modifications. Additional modifications include using a "L" amino acid in place of a "D" amino acid at the termini, cyclization of the peptide inhibitor, and amide rather than amino or carboxy termini to inhibit exopeptidase activity.

The peptides of the present invention may or may not be glycosylated. The peptides are not glycosylated, for example, when produced directly by peptide synthesis techniques or are produced in a prokaryotic cell transformed with a recombinant polynucleotide. Eukaryotically-produced peptide molecules are typically glycosylated.

Non-limiting examples of peptides in accordance with the present invention include those that maintain the sequence of a known GSK-3 substrate except for the substitution of the serine or threonine that is at the fourth position upstream of the phosphorylated serine or threonine (denoted as Z in the amino acid sequence described above). Preferably, Z is alanine. When the known substrate from which the inhibitor is derived is the CREB protein, the minimum size of the peptide is 10 residues, with the additional three residues all being upstream of the Z. Similarly, when the substrate from which the peptide is derived is heat shock factor-1 (HSF-1, the minimum number of residues in the peptide must be greater than seven. In addition, preferred peptides according to the present invention exclude glutamic acid at the $Y_3$ position.

Preferred polypeptides according to the present invention are those having an amino acid sequence as set forth in SEQ ID NO: 5, SEQ ID NO:8 or SEQ ID NO:9.

As used herein the phrase "hydrophobic moiety" refers to any substance or a residue thereof that is characterized by hydrophobicity. As is well accepted in the art, the term "residue" describes a major portion of a substance, which is covalently linked to another substance, herein the polypeptide described hereinabove.

Hence, a hydrophobic moiety according to the present invention is preferably a residue of a hydrophobic substance, and is covalently attached to the polypeptide described hereinabove. However, it would be appreciated that the hydrophobic moieties of the present invention can be attached to the polypeptide via any other interaction, such as, for example, hydrostatic interactions, Van der Wales interactions and the like.

Representative examples of hydrophobic substances from which the hydrophobic moiety of the present invention can be derived include, without limitation, substituted and unsubstituted, saturated and unsaturated hydrocarbons, where the hydrocarbon can be an aliphatic, an alicyclic or an aromatic compound and preferably includes at least 4 carbon atoms, more preferably at least 8 carbon atoms, more preferably at least 10 carbon atoms. Preferably, the hydrocarbon bears a functional group which enables its attachment to an amino acid residue. Representative examples of such a functional group include, without limitation, a free carboxylic acid ($C(=O)OH$), a free amino group ($NH_2$), an ester group ($C(=O)OR$, where R is alkyl, cycloalkyl or aryl), an acyl halide group ($C(=O)A$, where A is fluoride, chloride, bromide or iodide), a halide (fluoride, chloride, bromide or iodide), a hydroxyl group (OH), a thiol group (SH), a nitrile group ($C\equiv N$), a free C-carbamic group ($NR''-C(=O)-OR'$, where each of R' and R'' is independently hydrogen, alkyl, cycloalkyl or aryl), a free N-carbamic group ($OC(=O)-NR'-$, where R' is as defined above), a thionyl group ($S(=O)_2A$, where A is halide as defined above) and the like.

The hydrophobic moiety of the present invention can therefore comprise a residue of the hydrophobic substances described hereinabove.

The hydrophobic moiety of the present invention preferably comprises one or more fatty acid residue(s).

Preferred fatty acids that are usable in the context of the present invention include saturated or unsaturated fatty acids that have more than 10 carbon atoms, preferably between 12 and 24 carbon atoms, such as, but not limited to, myristic acid, lauric acid, palmitic acid, stearic acid, oleic acid, linoleic acid, linolenic acid, arachidonic etc., with myristic acid being presently the most preferred.

The hydrophobic moiety according to the present invention can be a fatty acid residue, or any other residue of hydrophobic substance as described above, per se, such that the fatty acid, or any other hydrophobic substance, is covalently attached directly to an amino acid residue of the polypeptide (via, for example, en ester bond or an amide bond). Alternatively, the hydrophobic moiety can be an amino acid residue that is modified to include a fatty acid residue, or any other residue of a hydrophobic substance as described hereinabove, such that this modified amino acid residue is attached to the polypeptide via a peptide bond or a substituted peptide bond, as is described hereinabove. Further alternatively, the hydrophobic moiety can be a short peptide in which one or more amino acid residues are modified to include a fatty acid residue or any other residue of a hydrophobic substance as described hereinabove. Such a peptide preferably includes between 2 and 15 amino acid residues and is attached to the polypeptide via a peptide bond or a substituted peptide bond, as is described hereinabove.

As an alternative to, or in combination with the hydrophobic moiety described above, the hydrophobic moiety, according to the present invention, can comprise a hydrophobic peptide sequence. The hydrophobic peptide sequence, according to the present invention, preferably includes between 2 and 15 amino acid residues, more preferably between 2 and 10 amino acid residues, more preferably between 2 and 5 amino acid residues, in which at least one amino acid residue is a hydrophobic amino acid residue.

Representative examples of hydrophobic amino acid residues include, without limitation, an alanine residue, a cysteine residue, a glycine residue, an isoleucine residue, a leucine residue, a valine residue, a phenylalanine residue, a tyrosine residue, a methionine residue, a proline residue and a tryptophan residue, or any modification thereof, as is described hereinabove.

Alternatively, the hydrophobic amino acid residue can include any other amino acid residue, which has been modified by incorporation of a hydrophobic moiety thereto.

In any event, the one or more hydrophobic moieties and the polypeptide are preferably selected such that the resulting conjugate of the present invention includes between 7 and 50 amino acid residues, preferably between 7 and 20 amino acid residues and more preferably between 10 and 13 amino acid residues.

The hydrophobic moiety or moieties of the present invention are preferably attached to one or more termini of the polypeptide, namely the N-terminus and/or the C-terminus of the polypeptide. However, since, as is discussed hereinabove, the C-terminus of the polypeptide includes a phosphrylated serine or threonine residue, which plays a crucial role in binding to the enzyme, it was postulated that attaching the hydrophobic moiety to the N-terminus of the polypeptide would be preferable.

Indeed, as is demonstrated in the Examples section that follows, conjugates in which the hydrophobic moiety is attached to the N-terminus of the polypeptide of the present invention, were found to be highly potent GSK-3 inhibitors.

These results can be explained by the recently published crystallization data of GSK-3, described by Dajani et al. (2001). The crystallization data of Dajani et al. showed that GSK-3 is crystallized as a dimer, suggesting that this dimerization has biological relevance. The catalytic region (residues 216-220) of one monomer (a) appears to interact with the N-terminus of an α-helix (residues 262-273) of the other monomer (b). This interaction of the two monomers (a) and (b) forms a hydrophobic patch in monomer (b).

Based on this crystallization data and the surprising discovery by the present inventor, it is believed, without being bound to any particular theory, that the hydrophobic moiety of the conjugates of the present invention interacts with this hydrophobic patch in monomer (b) and consequently improves the interaction of the peptide inhibitor with GSK-3, leading to an enhanced inhibitory effect.

Thus, according to the present invention, any other hydrophobic moiety, apart from those described above, that is structurally suitable for interacting with the hydrophobic patch on monomer (b) of the GSK-3 dimer, can be attached to the polypeptide described above.

As is demonstrated in the Examples section that follows, the conjugates of the present invention exhibit both high specificity and inhibitory effect toward GSK-3.

As is discussed hereinabove, the specificity of these conjugates is derived from the unique recognition motif of GSK-3, which, unlike other kinases, includes a phosphorylated serine or threonine residue, and the fact that the sequence of the polypeptide portion thereof is based on this recognition motif. As is demonstrated in the Examples section that follows, this feature renders the conjugates of the present invention substrate competitive inhibitors, and thus more specific as compared with other protein kinase inhibitors that are typically ATP competitive compounds.

The high inhibitory activity of the conjugates of the present invention is derived from both, the replacement of the phosphorylated residue at the Z position by a non-phosphorylated residue, which renders the enzyme inactive in phosphorylation, and the incorporation of the hydrophobic moiety/moieties, which provides for a better membrane permeability of the conjugate as well as for a better interaction with the hydrophobic patch of the enzyme.

Hence, according to another aspect of the present invention, there is provided a method of inhibiting an activity of GSK-3, which is effected by contacting cells expressing GSK-3 with an effective amount of the conjugate of the present invention.

As used herein, the term "effective amount" is the amount determined by such considerations as are known in the art, which is sufficient to inhibit the activity of GSK-3.

As is demonstrated in the Examples section that follows, a representative example of a conjugates according to the present invention strongly inhibits GSK-3, with an $IC_{50}$ value of about 40 μM, as measured by in vitro kinase assay.

Hence, the effective amount of the conjugates of the present invention preferably ranges between about 1 micromolar and about 100 micromolar, more preferably between about 1 micromolar and about 50 micromolar, and most preferably between about 1 micromolar and about 20 micromolar.

As used herein the term "about" refers to ±10%.

As is further demonstrated in the Examples section that follows, the inhibition activity of the conjugates of the present invention was tested in both in vitro and in vivo assays. Thus, the method according to this aspect of the present invention can be effected by contacting the cells with the conjugates in vitro and in vivo.

As the conjugates of the present invention do not include the required phosphorylated residue (at the Z position), GSK-3, while being bound thereto, is rendered inactive in phosphorylation reactions. Thus, the method according to this aspect of the present invention preferably pertains to inhibition of the phosphorylation and/or autophosphorylation activity of GSK-3.

The method according to this aspect of the present invention can be further effected by contacting the cells with an additional active ingredient that is capable of altering an activity of GSK-3, as is detailed hereinbelow.

The inhibition of GSK-3 activity is a way to increase insulin activity in vivo. High activity of GSK-3 impairs insulin action in intact cells (Eldar-Finkelman et al, 1997). This impairment results from the phosphorylation of insulin receptor substrate-1 (IRS-1) serine residues by GSK-3. Studies performed in patients with type II diabetes (non-insulin dependent diabetes mellitus, NIDDM) show that glycogen synthase activity is markedly decreased in these patients, and that decreased activation of protein kinase B (PKB), an upstream regulator of GSK-3, by insulin is also detected (Shulman et al, (1990); Nikoulina et al, (1997); Cross et al, (1995). Mice susceptible to high fat diet-induced diabetes and obesity have significantly increased GSK-3 activity in epididymal fat tissue (Eldar-Finkelman et al, 1999). Increased GSK-3 activity expressed in cells resulted in suppression of glycogen synthase activity (Eldar-Finkelman et al, 1996).

Inhibition of GSK-3 activity therefore provides a useful method for increasing insulin activity in insulin-dependent conditions. This feature is further demonstrated in the Examples section that follows, which shows that treatment with the conjugates of the present invention resulted in improved glucose uptake and glucose tolerance.

Thus, according to another aspect of the present invention there is provided a method of potentiating insulin signaling, which is effected by contacting insulin responsive cells with an effective amount, as is defined hereinabove, of the conjugate of the present invention.

As used herein, the phrase "potentiating insulin signaling" includes an increase in the phosphorylation of insulin receptor downstream components and an increase in the rate of glucose uptake as compared with glucose uptake in untreated subjects or cells.

In the experiments conducted in this respect. (see, the Examples section hereinbelow), it was further found that there is a dose-dependent effect of the conjugates of the present invention in cells treated with a sub-optimal concentration of insulin, indicating a potential additive effect of the GSK-3 inhibitors with insulin.

Therefore, the method according to this aspect of the present invention is preferably effected by contacting cells, in vitro or in vivo, with both the conjugates of the present invention and insulin.

Potentiation of insulin signaling, in vivo, resulting from administration of the conjugates of the present invention, can be monitored as a clinical endpoint. In principle, the easiest way to look at insulin potentiation in a patient is to perform the glucose tolerance test. After fasting, glucose is given to a patient and the rate of the disappearance of glucose from blood circulation (namely glucose uptake by cells) is measured by assays well known in the art. Slow rate (as compared to healthy subject) of glucose clearance will indicate insulin resistance. The administration of a GSK-3 inhibitor such as a conjugate according to the present invention to an insulin-resistant patient increases the rate of glucose uptake as compared with a non-treated patient. The conjugate may be administered to an insulin resistant patient for a longer period of time, and the levels of insulin, glucose, and leptin in blood circulation (which are usually high) may be determined. Decrease in glucose levels will indicate that the conjugate potentiated insulin action. A decrease in insulin and leptin levels alone may not necessarily indicate potentiation of insulin action, but rather will indicate improvement of the disease condition by other mechanisms.

By strongly inhibiting GSK-3 activity and potentiating insulin signaling, the conjugates of the present invention may be effectively utilized for treating any biological condition that is associated with GSK-3.

Hence, according to another aspect of the present invention, there is provided a method of treating a biological condition associated with GSK-3 activity. The method, according to this aspect of the present invention, is effected by administering to a subject in need thereof a therapeutically effective amount of the conjugate of the present invention, described hereinabove.

The phrase "biological condition associated with GSK-3 activity" as used herein includes any biological or medical condition or disorder in which effective GSK-3 activity is identified, whether at normal or abnormal levels. The condition or disorder may be caused by the GSK-3 activity or may simply be characterized by GSK-3 activity. That the condition is associated with GSK-3 activity means that some aspect of the condition can be traced to the GSK-3 activity.

Herein, the term "treating" includes abrogating, substantially inhibiting, slowing or reversing the progression of a condition or disorder, substantially ameliorating clinical symptoms of a condition or disorder or substantially preventing the appearance of clinical symptoms of a condition or disorder. These effects may be manifested, for example, by a decrease in the rate of glucose uptake with respect to type II diabetes or by halting neuronal cell death with respect to neurodegenerative disorders, as is detailed hereinbelow.

The term "administering" as used herein describes a method for bringing the conjugate of the present invention and cells affected by the condition or disorder together in such a manner that the conjugate can affect the GSK-3 activity in these cells. The conjugates of the present invention can be administered via any route that is medically acceptable. The route of administration can depend on the disease, condition or injury being treated. Possible administration routes include injections, by parenteral routes, such as intravascular, intravenous, intra-arterial, subcutaneous, intramuscular, intratumor, intraperitoneal, intraventricular, intraepidural, intracerebroventicular or others, as well as oral, nasal, ophthalmic, rectal, topical, or by inhalation. Sustained release administration is also specifically included in the invention, by such means as depot injections or erodible implants. Administration can also be intra-articularly, intrarectally, intraperitoneally, intramuscularly, subcutaneously, or by aerosol inhalant. Where treatment is systemic, the conjugate can be administered orally or parenterally, such as intravenously, intramuscularly, subcutaneously, intraorbitally, intracapsularly, intraperitoneally or intracisternally, as long as provided in a composition suitable for effecting the introduction of the conjugate into target cells, as is detailed hereinbelow.

The phrase "therapeutically effective amount", as used herein, describes an amount administered to an individual, which is sufficient to abrogate, substantially inhibit, slow or reverse the progression of a condition associated with GSK-3 activity, to substantially ameliorate clinical symptoms of a such a condition or substantially prevent the appearance of clinical symptoms of such a condition. The GSK-3 activity can be a GSK-3 kinase activity. The inhibitory amount may be determined directly by measuring the inhibition of a GSK-3 activity, or, for example, where the desired effect is an effect on an activity downstream of GSK-3 activity in a pathway that includes GSK-3, the inhibition may be measured by measuring a downstream effect. Thus, for example where inhibition of GSK-3 results in the arrest of phosphorylation of glycogen synthase, the effects of the conjugate may include effects on an insulin-dependent or insulin-related pathway, and the conjugate may be administered to the point where glucose uptake is increased to optimal levels. Also, where the inhibition of GSK-3 results in the absence of phosphorylation of a protein that is required for further biological activity, for example, the tau protein, then the conjugate may be administered until polymerization of phosphorylated tau protein is substantially arrested. Therefore, the inhibition of GSK-3 activity will depend in part on the nature of the inhibited pathway or process that involves GSK-3 activity, and on the effects that inhibition of GSK-3 activity has in a given biological context.

The amount of the conjugate that will constitute an inhibitory amount will vary depending on such parameters as the conjugate and its potency, the half-life of the conjugate in the body, the rate of progression of the disease or biological condition being treated, the responsiveness of the condition to the dose of treatment or pattern of administration, the formulation, the attending physician's assessment of the medical situation, and other relevant factors, and in general the health of the patient, and other considerations such as prior administration of other therapeutics, or co-administration of any therapeutic that will have an effect on the inhibitory activity of the conjugate or that will have an effect on GSK-3 activity, or a pathway mediated by GSK-3 activity.

Although it is expected that the inhibitory amount will fall in a relatively broad range that can be determined through routine trials, a preferred therapeutically effective amount according to the present invention is selected so as to achieve, at the treated site, an amount of the conjugate that ranges between about 10 nmol and about 1000 nmol, preferably between about 10 nmol and about 500 nmol, more preferably between about 100 nmol and about 400 nmol.

As is discussed in detail hereinabove, GSK-3 is involved in various biological pathways and hence, the method according to this aspect of the present invention can be used in the treatment of a variety of biological conditions, as is detailed hereinunder.

GSK-3 is involved in the insulin signaling pathway and therefore, in one example, the method according this aspect of the present invention can be used to treat any insulin-dependent condition.

As GSK-3 inhibitors are known to inhibit differentiation of pre-adipocytes into adipocytes, in another example, the method of this aspect of the present invention can be used to treat obesity.

In yet another example, the method according to this aspect of the present invention can be used to treat diabetes and particularly, non-insulin dependent diabetes mellitus.

Diabetes mellitus is a heterogeneous primary disorder of carbohydrate metabolism with multiple etiologic factors that generally involve insulin deficiency or insulin resistance or both. Type 1, juvenile onset, insulin-dependent diabetes mellitus, is present in patients with little or no endogenous insulin secretory capacity. These patients develop extreme hyperglycemia and are entirely dependent on exogenous insulin therapy for immediate survival. Type II, or adult onset, or non-insulin-dependent diabetes mellitus, occurs in patients who retain some endogenous insulin secretory capacity, but the great majority of them are both insulin deficient and insulin resistant. Approximately 95% of all diabetic patients in the United States have non-insulin dependent, Type 11 diabetes mellitus (NIDDM), and, therefore, this is the form of diabetes that accounts for the great majority of medical problems. Insulin resistance is an underlying characteristic feature of NIDDM and this metabolic defect leads to the diabetic syndrome. Insulin resistance can be due to insufficient insulin receptor expression, reduced insulin-binding affinity, or any abnormality at any step along the insulin signaling pathway (see U.S. Pat. No. 5,861,266).

The conjugates of the present invention can be used to treat type II diabetes in a patient with type II diabetes as follows: a therapeutically effective amount of the conjugate is administered to the patient, and clinical markers, e.g., blood sugar level, are monitored. The conjugates of the present invention can further be used to prevent type II diabetes in a subject as follows: a prophylactically effective amount of the conjugate is administered to the patient, and a clinical marker, for example IRS-1 phosphorylation, is monitored.

Treatment of diabetes is determined by standard medical methods. A goal of diabetes treatment is to bring sugar levels down to as close to normal as is safely possible. Commonly set goals are 80-120 milligrams per deciliter (mg/dl) before meals and 100-140 mg/dl at bedtime. A particular physician may set different targets for the patent, depending on other factors, such as how often the patient has low blood sugar reactions. Useful medical tests include tests on the patient's blood and urine to determine blood sugar level, tests for glycated hemoglobin level ($HbA_{1c}$; a measure of average blood glucose levels over the past 2-3 months, normal range being 4-6%), tests for cholesterol and fat levels, and tests for urine protein level. Such tests are standard tests known to those of skill in the art (see, for example, American Diabetes Association, 1998). A successful treatment program can also be determined by having fewer patients in the program with diabetic eye disease, kidney disease, or nerve disease.

Hence, in one particular embodiment of the method according to this aspect of the present invention, there is provided a method of treating non-insulin dependent diabetes mellitus: a patient is diagnosed in the early stages of non-insulin dependent diabetes mellitus. A conjugate of the present invention is formulated in an enteric capsule. The patient is directed to take one tablet after each meal for the purpose of stimulating the insulin signaling pathway, and thereby controlling glucose metabolism to levels that obviate the need for administration of exogenous insulin As is further discussed hereinabove, it has been suggested that GSK-3 inhibition is associated with affective disorders. Therefore, in another example, the method according to this aspect of the present invention can be used to treat affective disorders such as unipolar disorders (e.g., depression) and bipolar disorders (e.g., manic depression). As is detailed hereinbelow, the anti-depressive effect of the conjugates of the present invention, as well as the effect thereof on up-regulation of β-catenin levels has been demonstrated, thus indicating, for the first time, a direct link between GSK-3 inhibitors and affective disorders.

As GSK-3 is also considered to be an important player in the pathogenesis of neurodegenerative disorders and diseases, the method according to this aspect of the present invention can be further used to treat a variety of such disorders and diseases.

In one example, since inhibition of GSK-3 results in halting neuronal cell death, the method according to this aspect of the present invention can be used to treat a neurodegenerative disorder that results from an event that cause neuronal cell death. Such an event can be, for example, cerebral ischemia, stroke, traumatic brain injury or bacterial infection.

In another example, since GSK-3 activity is implicated in various central nervous system disorders and neurodegenerative diseases, the method according to this aspect of the present invention can be used to treat various chronic neurodegenerative diseases such as, but not limited to, Alzheimer's disease, Huntington's disease, Parkinson's disease, AIDS associated dementia, amyotrophic lateral sclerosis (AML) and multiple sclerosis.

As is discussed hereinabove, GSK-3 activity has particularly been implicated in the pathogenesis of Alzheimer's disease. Hence, in one representative embodiment of the method according to this aspect of the present invention, there is provided a method of treating a patient with Alzheimer's disease: A patient diagnosed with Alzheimer's disease is administered with a conjugate of the present invention, which inhibits GSK-3-mediated tau hyperphosphorylation, prepared in a formulation that crosses the blood brain barrier (BBB). The patient is monitored for tau phosphorylated polymers by periodic analysis of proteins isolated from the patient's brain cells for the presence of phosphorylated forms of tau on an SDS-PAGE gel known to characterize the presence of and progression of the disease. The dosage of the conjugate is adjusted as necessary to reduce the presence of the phosphorylated forms of tau protein.

GSK-3 has also been implicated with respect to psychotic disorders such as schizophrenia, and therefore the method according to this aspect of the present invention can be further used to treat psychotic diseases or disorders, such as schizophrenia.

It should be noted that the conjugates of the present invention are particularly advantageous in the treatment of affective and neurodegenerative diseases or disorders since, apart from exerting enhanced inhibition activity of GSK-3 and enhanced membrane permeability, it is postulated that the inclusion of a hydrophobic moiety within the conjugates further provides for enhanced lipophilicity of the conjugates and, as a result, for enhanced permeability through the blood brain barrier (BBB). This enhanced permeability may allow a systemic, rather than local, administration of the conjugates, such that the need to administer the inhibitors intracerebroventicularly (icv) is avoided.

The method according to this aspect of the present invention can be further effected by co-administering to the subject one or more additional active ingredient(s) which is capable of altering an activity of GSK-3.

As used herein, "co-administering" describes administration of a conjugate according to the present invention in combination with the additional active ingredient(s) (also referred to herein as active or therapeutic agent). The additional active agent can be any therapeutic agent useful for treatment of the patient's condition. The co-administration may be simultaneous, for example, by administering a mixture of the conjugate and the therapeutic agents, or may be accomplished by administration of the conjugate and the active agents separately, such as within a short time period. Co-administration also includes successive administration of the conjugate and one or more of another therapeutic agent. The additional therapeutic agent or agents may be administered before or after the conjugate. Dosage treatment may be a single dose schedule or a multiple dose schedule.

As is discussed hereinabove and is further demonstrated in the Examples section that follows, co-treatment of cells with the conjugates of the present invention and insulin resulted in an additive effect with respect to glucose uptake, and therefore the additional active ingredient can be insulin.

Preferably, the additional active ingredient is capable of inhibiting an activity of GSK-3, such that the additional active ingredient according to the present invention can be any GSK-3 inhibitor other than the conjugates of the present invention, e.g., lithium, valproic acid and lithium ion.

Alternatively, the additional active ingredient can be an active ingredient that is capable of downregulating an expression of GSK-3.

An agent that downregulates GSK-3 expression refers to any agent which affects GSK-3 synthesis (decelerates) or degradation (accelerates) either at the level of the mRNA or at the level of the protein. For example, a small interfering polynucleotide molecule which is designed to down regulate the expression of GSK-3 can be used as an additional active ingredient according to this embodiment of the present invention.

An example for a small interfering polynucleotide molecule which can down-regulate the expression of GSK-3 is a small interfering RNA or siRNA, such as, for example, the morpholino antisense oligonucleotides described by in Munshi et al. (Munshi C B, Graeff R, Lee H C, *J Biol Chem* 2002 Dec 20; 277(51): 49453-8), which includes duplex oligonucleotides which direct sequence specific degradation of mRNA through the previously described mechanism of RNA interference (RNAi) (Hutvagner and Zamore (2002) Curr. Opin. Genetics and Development 12:225-232).

As used herein, the phrase "duplex oligonucleotide" refers to an oligonucleotide structure or mimetics thereof, which is formed by either a single self-complementary nucleic acid strand or by at least two complementary nucleic acid strands. The "duplex oligonucleotide" of the present invention can be composed of double-stranded RNA (dsRNA), a DNA-RNA hybrid, single-stranded RNA (ssRNA), isolated RNA (i.e., partially purified RNA, essentially pure RNA), synthetic RNA and recombinantly produced RNA.

Preferably, the specific small interfering duplex oligonucleotide of the present invention is an oligoribonucleotide composed mainly of ribonucleic acids.

Instructions for generation of duplex oligonucleotides capable of mediating RNA interference are provided in www.ambion.com.

Hence, the small interfering polynucleotide molecule according to the present invention can be an RNAi molecule (RNA interference molecule).

Alternatively, a small interfering polynucleotide molecule can be an oligonucleotide such as a GSK-3-specific antisense molecule or a rybozyme molecule, further described hereinunder.

Antisense molecules are oligonucleotides, which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target polynucleotide. An additional region of the oligonucleotide may serve as a substrate for enzymes capable of cleaving RNA:DNA or RNA:RNA hybrids. An example for such includes RNase H, which is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

The antisense molecules of the present invention may be formed as composite structures of two or more oligonucleotides, modified oligonucleotides, as described above. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein fully incorporated by reference.

Rybozyme molecules are being increasingly used for the sequence-specific inhibition of gene expression by the cleavage of mRNAs. Several rybozyme sequences can be fused to the oligonucleotides of the present invention. These sequences include but are not limited ANGIOZYME specifically inhibiting formation of the VEGF-R (Vascular Endothelial Growth Factor receptor), a key component in the angiogenesis pathway, and HEPTAZYME, a rybozyme designed to selectively destroy Hepatitis C Virus (HCV) RNA, (Rybozyme Pharmaceuticals, Incorporated-WEB home page).

Further alternatively, a small interfering polynucleotide molecule, according to the present invention can be a DNAzyme.

DNAzymes are single-stranded catalytic nucleic acid molecules. A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M Curr Opin Mol Ther 2002; 4:119-21).

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 20002, Abstract 409, Ann Meeting Am Soc Gen Ther www.asgt.org). In another application, DNAzymes complementary to bcr-abl oncogenes were successful in inhibiting the oncogenes expression in leukemia cells, and lessening relapse rates in autologous bone marrow transplant in cases of CML and ALL.

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art.

While continuing to evaluate the inhibition activity of the conjugates of the present invention, experiments were conducted with respect to the therapeutic effect of these conjugates on affective disorders. As is detailed and manifested in the Examples section that follows, during these experiments it was surprisingly found that the conjugates of the present invention clearly exhibit anti-depressive activity.

Hitherto, the only link between GSK-3 and affective disorders was based on the findings that some mood stabilizers such as lithium are GSK-3 inhibitors. However, no link or evidence, which demonstrates a direct relation between affective disorders and GSK-3 activity, has been shown. Furthermore, it is known that lithium, as well as other mood stabilizers, affect multiple signaling pathways, and inhibit other cellular targets (Berridge et al., 1989; Phiel and Klein, 2001), and are therefore not specific inhibitors of GSK-3, as opposed to the conjugates of the present invention. The findings of the present invention therefore indicate for the first time that specific inhibitors of GSK-3 can serve as potent and efficacious agents for treating affective disorders.

Thus, according to another aspect of the present invention there is provided a method of treating an affective disorder in a subject in need thereof, which is effected by administering to the subject a therapeutically effective amount of one or more compound(s) that is capable of specifically inhibiting an activity of GSK-3.

The experiments conducted in this respect further demonstrated that administration of specific GSK-3 inhibitors, such as the conjugates of the present invention, resulted in up-regulation of the β-catenin level in the hippocampus of treated animals.

Therefore, according to yet another aspect of the present invention, there is provided a method of up-regulating a β-catenin level in a hippocampus of a subject, which is effected by administering to the subject an effective amount of one or more compound(s) that is capable of specifically inhibiting an activity of GSK-3.

The phrase "specifically inhibiting", as used herein, refers to compounds that are characterized by high affinity only toward GSK-3, and thus have a diminished, if any, affinity toward other kinases.

As is described hereinabove, polypeptides that are based on the recognition motif of GSK-3 are highly specific GSK-3 inhibitors. The results presented in Table 4 in the Examples section that follows clearly demonstrate the inability of a representative example of such a polypeptide to inhibit protein kinases other than GSK-3.

Hence, the methods according to these aspects of the present invention are preferably effected using a polypeptide that has the amino acid sequence:

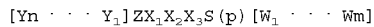

wherein, m equals 1 or 2; n is an integer from 1 to 50; S(p) is a phosphorylated serine residue or a phosphorylated threonine residue; Z is any amino acid residue excepting serine residue or threonine residue; and $X_1$, $X_2$, $X_3$, $Y_1$-$Y_n$ and $W_1$-$W_m$ are each independently any amino acid residue, as is described in detail hereinabove.

More preferably, the compound is the conjugate of the present invention.

While being highly efficient therapeutic agents, and since therapeutic applications often require administration of effective amounts of an active ingredient to a treated individual, the conjugate of the present invention is preferably included, as an active ingredient, in a pharmaceutical composition which further comprises a pharmaceutically acceptable carrier for facilitating administration of the conjugate to the treated individual and possibly to facilitate entry of the active ingredient into the targeted tissues or cells.

Hence, according to an additional aspect of the present invention there is provided a pharmaceutical composition which comprises, as an active ingredient, the conjugate of the present invention and a pharmaceutically acceptable carrier.

Hereinafter, the phrases "pharmaceutically acceptable carrier" and "physiologically acceptable carrier" refer to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The pharmaceutical acceptable carrier can further include other agents such as, but not limited to, absorption delaying agents, antibacterial agents, antifungal agents, antioxidant agents, binding agents, buffering agents, bulking agents, cationic lipid agents, coloring agents, diluents, disintegrants, dispersion agents, emulsifying agents, excipients, flavoring agents, glidants, isotonic agents, liposomes, microcapsules, solvents, sweetening agents, viscosity modifying agents, wetting agents, and skin penetration enhancers.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasal, or intraocular injections.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the conjugate into preparations which can be used pharmaceutically. The composition can be formulated in a delivery form such as an aerosol delivery form, aqueous solution, bolus, capsule, colloid, delayed release, depot, dissolvable powder, drops, emulsion, erodible implant, gel, gel capsule, granules, injectable solution, ingestible solution, inhalable solution, lotion, oil solution, pill, suppository, salve, suspension, sustained release, syrup, tablet, tincture, topical cream, transdermal delivery form. Proper formulation is dependent upon the route of administration chosen.

For injection, the conjugate of the invention may be formulated in aqueous solutions, preferably in physiologically compatible buffers such as Hank's solution, Ringer's solution, or physiological saline buffer with or without organic solvents such as propylene glycol, polyethylene glycol. For transmucosal administration, penetrants are used in the formulation. Such penetrants are generally known in the art.

For oral administration, the conjugate can be formulated readily by combining the conjugate with pharmaceutically acceptable carriers well known in the art. Such carriers enable the conjugate of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the conjugate according to the present invention is conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the ingredient and a suitable powder base such as lactose or starch.

The conjugate described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the conjugate in water-soluble form. Additionally, suspensions of the conjugate may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredient to allow for the preparation of highly concentrated solutions.

Alternatively, the conjugate may be in powder form for constitution with a suitable vehicle, e.g., sterile, pyrogen-free water, before use.

The conjugate of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the conjugate is contained in an amount effective to achieve the intended purpose. More specifically, a therapeutically effective amount means an amount of a conjugate effective to affect symptoms of a condition or prolong the survival of the subject being treated.

Determination of a therapeutically effective amount is well within the capability of those skilled in the art, especially in light of the detailed disclosure provided herein.

For any active ingredient used in the methods of the invention, the therapeutically effective amount or dose can be estimated initially from activity assays in cell cultures and/or animals. Such information can be used to more accurately determine useful doses in humans.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Compositions of the present invention may, if desired, be presented in a pack or dispenser device, such as a FDA approved kit, which may contain one or more unit dosage forms containing the conjugate. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a conjugate of the invention formulated in a compatible pharmaceutical carrier may also be prepared, placed in an appropriate container, and labeled for treatment of an indicated condition. Suitable conditions indicated on the label may include, for example, any of the biological conditions associated with GSK-3 activity listed hereinabove.

Hence, the pharmaceutical composition of the present invention can be packaged in a packaging material and identified in print, on or in the packaging material, for use in the treatment or prevention of a biological condition associated with GSK-3.

The pharmaceutical composition of the present invention can further comprises an additional active ingredient that is capable of interfering with an activity of GSK-3, as is described hereinabove.

Further according to the present invention, there is provided a process of preparing the conjugates of the present invention, which comprises providing the polypeptide described hereinabove, providing one or more hydrophobic moiety or moieties as described hereinabove, and conjugating said the hydrophobic moiety or moieties and the polypeptide.

In one embodiment, the polypeptide of the present invention is provided by a chemical synthesis, using well known chemical procedures, such as solution or solid-phase peptide synthesis, or semi-synthesis in solution beginning with protein fragments coupled through conventional solution methods, as described by Dugas et al (1981). The polypeptide of the invention can be chemically synthesized, for example, by the solid phase peptide synthesis of Merrifield et al (1964). Alternatively, a peptide inhibitor of the invention can be synthesized using standard solution methods (see, for example, Bodanszky, 1984). Newly synthesized peptides can be purified, for example, by high performance liquid chromatography (HPLC), and can be characterized using, for example, mass spectrometry or amino acid sequence analysis.

Alternatively, the. polypeptides of the invention can be provided recombinantly. Systems for cloning and expressing the polypeptide of the invention include various microorganisms and cells that are well known in recombinant technology. These include, for example, various strains of *E. coli, Bacillus, Streptomyces*, and *Saccharomyces*, as well as mammalian, yeast and insect cells. The polypeptide of the invention can be produced as a peptide or fusion protein. Suitable vectors for producing the peptide inhibitor are known and available from private and public laboratories and depositories and from commercial vendors. See Sambrook et al, (1989). Recipient cells capable of expressing the gene product are then transfected. The transfected recipient cells are cultured under conditions that permit expression of the recombinant gene products, which are recovered from the culture. Host mammalian cells, such as Chinese Hamster ovary cells (CHO) or COS-1 cells, can be used. These hosts can be used in connection with poxvirus vectors, such as vaccinia or swinepox. Suitable non-pathogenic viruses that can be engineered to carry the synthetic gene into the cells of the host include poxviruses, such as vaccinia, adenovirus, retroviruses and the like. A number of such non-pathogenic viruses are commonly used for human gene therapy, and as carrier for other vaccine agents, and are known and selectable by one of skill in the art. The selection of other suitable host cells and methods for transformation, culture, amplification, screening and product production and purification can be performed by one of skill in the art by reference to known techniques (see, e.g., Gething et al, 1981).

Once the polypeptide is provided, the hydrophobic moiety or moieties can be conjugated thereto by commonly used techniques. For example, in cases where the hydrophobic moiety is a fatty acid, techniques for adding a fatty acid (e.g., myristic acid) to an amino acid residue within the polypeptide sequence are used. Alternatively, an amino acid residue is modified to include a hydrophobic moiety such as fatty acid and is thereafter attached to the polypeptide by known chemical procedures, as is described hereinabove.

In cases where the hydrophobic moiety comprises a hydrophobic peptide sequence, the hydrophobic peptide can be prepared using the methods described hereinabove and thereafter be conjugated to the polypeptide. Alternatively, the conjugate can be prepared recombinantly, using systems, as described hereinabove, for cloning and expressing a fused polypeptide that comprises the polypeptide of the present invention and such a hydrophobic peptide sequence.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Experimental Methods

Materials:

All the peptides, including conjugates having a hydrophobic moiety attached to a peptide, were synthesized by Genemed Synthesis Inc. (San Francisco, Calif.).

Radioactive materials were purchased from Amersham Ltd.

Cyclic dependent protein kinase, cdc2, casein kinase-2 (CK-2), CK-2 peptide, catalytic subunit of cAMP dependent protein kinase (PKA), and mitogen activated protein kinase (MAPK) were purchased from New England BioLabs (Beverly, Mass.)

All other reagents were obtained from Sigma (Israel).

Peptide inhibitors were dissolved in 50 mM HEPES buffer, pH 7.5.

Myristoylated peptides (mts) were dissolved in 0.1% DMSO buffer solution.

In Vitro Studies:

In vitro inhibition assays: Purified recombinant rabbit GSK-3β (Eldar-Finkelman et al., 1996) was incubated with peptide substrate PGS-1 (YRRAAVPPSPSLSRHSSPSQS(p)EDEEE) (SEQ ID NO:15) and with a peptide inhibitor at indicated concentrations. The reaction mixture included Tris 50 mM (pH=7.3), 10 mM MgAc, $^{32}$P[γ-ATP] (100 μM), 0.01% β-mercaptoethanol, and was incubated for 10 minutes at 30° C. Reactions were spotted on phosphocellulose paper (p81), washed with 100 mM phosphoric acid, and counted for radioactivity (as described in Eldar-Finkelman et al., 1996).

The effect of L803 (200 μM) on other protein kinases was tested by incubating Cdc2 (1 unit) with a reaction mixture similar to that described hereinabove and containing histone H1 substrate (5 μg). The reactions were boiled with SDS sample buffer, separated on gel electrophoresis and autoradiographed.

MAPK, PKA and CK-2 activities were examined at similar conditions except that nyelin basic protein (MBP, a gift from Zvi Naor), p9CREB (Table 3), and CK-2 peptide were used as substrates, respectively.

Protein kinase C-δ was immunoprecipitated with a specific antibody (Santa Cruz, Calif.) from fat tissue extracts and its activity was measured at similar conditions except that the lipid cofactor phosphatidylserine (40 μM) was included together with histone H1 as a substrate.

Protein kinase B (PKB) was immunoprecipitated from extracts of serum-stimulated NIH/3T3 cells with a specific antibody (New-England BioLabs, Mass.) and the kinase assays were performed at similar conditions except that MBP was used as a substrate.

Glycogen synthase activity in HEK 293 cells: To test the impact of the conjugates of the present invention in intact cells, the membrane preamble L803 inhibitor L803-mts (N-Myristol-GKEAPPAPPQS(p)P) (SEQ ID NO:16) and two similarly modified respective controls LE803-mts (N-Myristol-GKEAPPAPPQSEP) (SEQ ID NO:17) and LS803-mts (N-Myristol-GKEAPPAPPQSP) (SEQ ID NO:18), in which the phosphorylated serine was replaced with glutamic acid (that usually mimics a phosphorylated group) or a serine residue, respectively, were designed and synthesized. In vitro assays were performed to confirm that the two control conjugates LE803-mts and LS803-mts, do not inhibit GSK-3 (data not shown).

HEK 293 cells were grown in 10 cm plates with Dulbecco's modified Eagle medium (DMEM) supplemented with 10% fetal calf serum (FCS). On the day of the experiment, cells were incubated with low glucose medium supplemented with 0.5% FCS for 1 hour, followed by the addition of the conjugate L803-mts or its respective controls LE803-mts and LS803-mts at various concentrations, for additional 2.5 hours. A vehicle control of DMSO (0.1% DMSO) was also tested. Cells were thereafter washed twice with ice-cold GS buffer (50 mM Tris, pH=7.8, 100 mM NaF, 10 mM EDTA with protease inhibitors: 20 μg/ml leupeptine, 10 μg/ml aprotinine, 10 mg/ml pepstatin A, 1 mM benzamidine), scraped with the same buffer, and frozen in liquid nitrogen (as described in Eldar-Finkelman et al., 1996). Glycogen synthase activity was assayed according to the method of Thomas et al. (1968), based on the incorporation of uridine 5-diphosphate [$^{14}$C] glucose (UDPG) into glycogen. Aliquots of cell lysates (15 μl) were incubated with 15 μl reaction mixture (66.6 mM Tris, pH=7.8, 32.5 mM KF, 0.8 μCi/μl [$^{14}$C]-UDPG (400 μM), 13 mg/ml glycogen rabbit liver, Sigma) for 20 minutes at 30° C. (as described in Eldar-Finkelman et al., 1996). The reactions were then spotted on ET31 (Whatman) papers, washed with 66% ice-cold ethanol, and counted for radioactivity. Glycogen synthase assays were measured in the presence of 0.1 mM glucose-6-phosphate (G6P). Similar results were obtained when G6P was absent in the assays (data not shown).

Glucose uptake in isolated adipocytes: Mice adipocytes were isolated from epididymal fat pad by digestion with 0.8 mg/ml collagenase (Worthington Biochemical) as described previously (Lawrence et al., 1977). Digested fat pads were passed through nylon mesh and cells were washed 3 times with Krebs-bicarbonate buffer (pH=7.4) containing 1% bovine serum albumin (Fraction V, Boehringer Mannheim, Germany), 10 mM HEPES (pH=7.3), 5 mM glucose and 200 nM adenosine. Cells were incubated with L803-mts or LE803-mts at indicated concentrations for 1 hour, followed by addition of 2-deoxy [$^3$H] glucose (0.5 μci/vial) for 10 minutes. The assay was terminated by centrifugation of cells through dinonylphthalate (ICN, USA). $^3$H was thereafter quantitated by liquid scintillation analyzer (Packard). Non-specific uptake of 2-deoxy-[$^3$H] glucose was determined by the addition of cytochalasin B (50 μM) 30 minutes prior to the addition of radioactive material.

In another set of experiments, adipocytes were treated with various concentrations of L803-mts 1 hour before addition of sub-optimal concentration of insulin (5 nM). Glucose uptake was determined as described above.

In Vivo Studies:

High fat diet-induced diabetes in animals: 4 weeks C57Bl/6J mice received high fat diet containing 35% lard (Bioserve, Frenchtown, N.J.) with 55% of calories from fat as previously described (Surwit et al., 1988). Animals were housed in individual cages with free access to water in a temperature-controlled facility with 12 hours light/dark cycle. Animals developed obesity hyperglycemia and hyperinsulinemia after 16 weeks of diet feeding (I. Talior, unpublished results).

Glucose tolerance tests: Glucose tolerance tests were performed in overnight fasted C57Bl/6J mice (12 hours). L803-mts or LE803-mts were administrated intraperitoneally (i.p.) to mice (400 nmol peptide), glucose (1 gram/kg) was injected i.p. one hour thereafter and blood samples were collected from tail vein at various time points. Blood glucose levels were immediately measured by Sugar Accutrend Sensor, (Roche, Germany)).

Similar experiments were performed in diabetic C57Bl/6J mice that were fed high fat diets for 16 weeks as is described hereinabove, except that mice fasted for 6 hours prior to administration, and L803-mts was injected 90 minutes prior to glucose injection.

Forced Swimming Test (FST): C57BL/6J mice were housed in individual cages with free access to water in a temperature-controlled facility with a 12 hours light/dark cycle. Animals at age 14-16 weeks were used, and each experimental group consisted of randomly chosen 10-20 mice. At day one, mice were subjected to pre-FST (see below). At day two, mice were anesthetized with halothane (inhalation) and were unilaterally intracerebroventricularly injected (i.c.v., 1 μl of 25 mM stock solution) with L803-mts or a scrambled control peptide (cpL803-mts). Animals were subjected to FST once 1, 3, and 12 hours after reagents were administrated. The FST procedure used was similar to that initially described by Porsolt et al. (1977). Briefly, animals were placed at day one in a large cylinder (30 cm×45 cm) of 25° C. water for a 15-minutes period. At day two (24 hours later), treated mice were placed in the cylinder of water for a 6-minutes period. The duration of immobility was monitored during the last 4 minutes of the 6-minute test. Immobility period was defined as the time spent by the animal floating in the water without struggling and making only those movements necessary to keep its head above the water. All testing took place between 11:00 and 15:00. After completion the FST, mice were scarified, and hippocampuses were removed, frozen in liquid nitrogen, and stored at −80° C. Animal care followed the institutional animal care and used committee.

Hippocampus extracts: Hippocampus tissue was homogenized with ice cold buffer H (50 mM β-glycerophosphate pH=7.3, 10% glycerol, 1 mM EGTA, 1 mM EDTA, 10 mM NaF, 5 mM NaPPi, 25 μg/ml leupeptin, 25 μg/ml aprotinin, 500 nM microcystine LR and 1% Triton X100). The extracts were centrifuged for 20 minutes at 15,000×g, and supernatants were collected. Equal amounts of proteins (30 μg) as determined by Bradford analysis (Bradford, 1796) were boiled with Laemmli sample buffer and subjected to gel electrophoresis (10% polyacrylamide gel), transferred to nitrocellulose membranes, and immunoblotted with specific monoclonal antibodies for β-catenin (Transduction laboratories, USA).

Statistics:

Graphics and statistical analyses were performed using one-factor analysis of variance (ANOVA) using Origin Professional 6.0. Data were deemed significant when P<0.05. Data are expressed as group mean with standard errors.

Experimental Results

In Vitro Studies:
In Vitro Inhibition Assays:
Based on the theory set forth in PCT/US01/00123, a set of phosphorylated peptide inhibitors was designed, synthesized and their activity was evaluated by the in vitro analyses described above. The set of inhibitors as well as the analyses results are presented in Table 3 below.

and 4, respectively) eliminated the capacity of GSK-3 to phosphorylate these peptides, thus indicate the same requirement for a substrate. Moreover, reducing peptide length to the minimum sequence of $SX_1X_2X_3S(p)$ (SEQ ID NO:19), also eliminated the inhibitory capacity of the peptide (Table 3, peptides 6 and 12-14), suggesting that additional residues flanking this motif (apparently at least one to two at each end) must be included in the peptide inhibitor. Notably, inhibition was improved when the glutamic acid positioned upstream to

TABLE 3

| No. Peptide | SEQ ID NO: | Length | Substrate functionality | Inhibitor functionality | Comments |
|---|---|---|---|---|---|
| 1 KRREILS$^1$RRPS$^2$(p)YR | SEQ ID NO: 1 | 13 | + | − | derived from CREB |
| 2 ILSRRPS(p)YR | SEQ ID NO: 2 | 9 | + | − | p9CREB |
| 3 ILSRPPEYR | SEQ ID NO: 3 | 9 | − | − | |
| 4 ILSRPPY(p)YR | SEQ ID NO: 4 | 9 | − | − | |
| 5 KRREILARRPS(p)YR | SEQ ID NO: 5 | 13 | − | + | Hz13 |
| 6 ILARRPS(p)YR | SEQ ID NO: 6 | 10 | − | * | |
| 7 KEEPPSPPQS(p)P | SEQ ID NO: 7 | 11 | + | − | Derived from Heat shock factor-1 |
| 8 KEEPPAPPQS(p)P | SEQ ID NO: 8 | 11 | − | + | pAHSF |
| 9 KEAPPAPPQS(p)P | SEQ ID NO: 9 | 11 | − | + | L803 |
| 10 KEEPPAPPQSP | SEQ ID NO: 10 | 11 | − | − | |
| 11 KEEPPAPPQEP | SEQ ID NO: 11 | 11 | − | − | |
| 12 PAPPQS(p)P | SEQ ID NO: 12 | 7 | − | * | |
| 13 EPPAPRRE | SEQ ID NO: 13 | 8 | − | − | |
| 14 EPPAPR | SEQ ID NO: 14 | 6 | − | − | |

S(p) denotes phosphorylated serine;
Replacement of S$^1$ by alanine is marked bold;
* weak inhibition activity (IC50 > 800 μM).

The results indicate that the replacement of S$^1$ with alanine in two known peptide sequences derived from GSK-3 substrates—CREB (cAMP responsive element binding protein) and HSF-1 (heat shock factor-1)—converted the substrates into inhibitors (Table 3, 5 and 8). Replacement of the glutamic acid located upstream to S$^1$ in pAHSF peptide improved the inhibition potency (L803, Table 3, peptide 9).

Replacing the S$^2$(p) with either glutamic acid, which often mimics a phosphorylated group, or with serine itself (Table 3, peptides 10 and 11, respectively), rendered these peptides inactive inhibitors, thus indicating that a phosphorylated serine is an absolute requirement for a peptide inhibitor. Replacement of S$^2$(p) in the p9CREB peptide substrate with glutamic acid or phosphorylated tyrosine (Table 3, peptides 3

S$^1$ was replaced with alanine (see, peptide 8, L803, versus peptide 9, pAHSF). Apparently, a glutamic residue is found in a similar position in some (but not all) GSK-3 substrates, including eIF2B, CREB c-Myc, and D-Jun (Woodgett, 2001), a feature which may point to a critical role for this residue in enzyme/substrate interaction and/or dissociation.

Figure 1B:
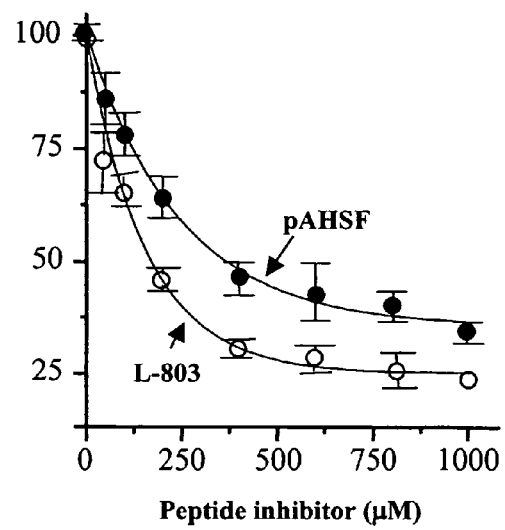

FIGS. 1a and 1b present the inhibition curves of three of the tested peptide inhibitors (Table 3, peptides 5, 8 and 9)—Hz13 (FIG. 1a), pAHSF and L803 (FIG. 1b). The IC50 values obtained for these the other tested inhibitors (data not shown) were in the range of 150-330 μM, with L803 having the most promising IC50 value of 150 μM.

Figure 2:
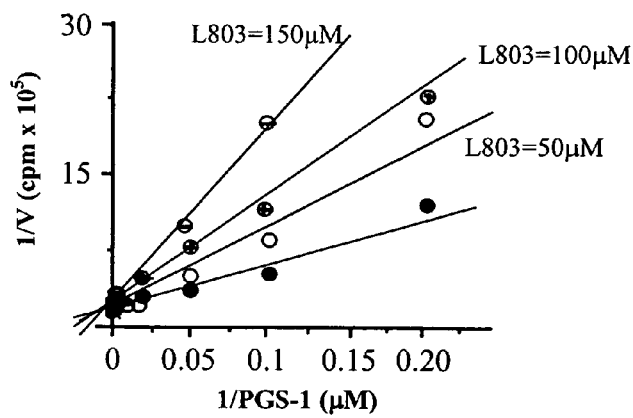
FIG. 2 is a Lineweaver-Burk plot presenting the inhibition of GSK-3 by L803 at indicated concentrations and demonstrating that the GSK-3 peptide inhibitor is a competitive specific inhibitor. The results represent phosphate incorporation into PGS-1 peptide substrate (CPM). Results show one representative experiment out of 4. Each point is a mean of duplicate samples. Calculated $K_i=70\pm10$ µM.

The kinetic nature of the peptide inhibitors was studied by measuring the initial velocity as a function of the substrate concentration at several inhibitor concentrations. Lineweaver-Burk plots of the GSK-3 inhibition by these inhibitors confirmed the assumption that these are substrate-competitive inhibitors (data not shown). FIG. 2 presents the Lineweaver-Burk plot of the GSK-3 inhibition by L803, as an exemplary inhibitor.

L803, which was found to be the most potent inhibitor for GSK-3, was selected as a representative peptide inhibitor for further studies.

Thus, the specificity of L803 was tested by examining the ability of several protein kinases to phosphorylate their substrates in the presence of this peptide inhibitors. The results, by way of the percent of the activity measured in the absence of the inhibitor, are presented in Table 4, indicating the inability of L803 (at a 200 µM concentration) to significantly inhibit a selection of protein kinases other than GSK-3. Notably, even the most closely related protein kinase to GSK-3, cycling dependent protein kinase (cdc2), was not inhibited by L803, further supporting the specificity of our inhibitor.

TABLE 4

| Protein kinase | % Maximal activity |
| --- | --- |
| MAPK | 106 |
| PKA | 86 |
| CK-2 | 117 |
| Cdc2 | 90 |
| PKC-δ | 111 |
| PKB | 91 |

The inhibition kinetics of a representative example of a conjugate that includes a peptide inhibitor and a hydrophobic moiety covalently linked thereto was evaluated by performing the assays described above with a myristolated L803, termed L803-mts, a L803-mts inhibitor to which myristic acid was attached to its N-terminus.

As is shown in FIGS. 3a and 3b, this modification substantially reduced the IC50 value of the inhibitor to 40 µM, suggesting that addition of a hydrophobic moiety to a GSK-3 inhibitor provides for improved inhibition.

A comparative GSK-3β inhibition assay was performed as described above using L803-mts and a scrambled control peptide termed cpL803-mts. As is shown in FIG. 4, L803-mts inhibited GSK-3β (IC50=40 µM). In contrast, cpL803-mts did not inhibit GSK-3β activity at the range of concentrations tested (0-300 µM).

Glycogen Synthase Activity in HEK 293 Cells:

To test the biological effects of the myristolated peptide in intact cells and in animals, L803-mts and two similarly modified respective controls, LE803-mts and LS803-mts, were used. The effect of L803-mts on a known physiological target of GSK-3, glycogen synthase, which is inhibited upon phosphorylation by GSK-3 (Wang et al., 1993; Woodgett et al., 1984), was first studied.

Figure 5A:
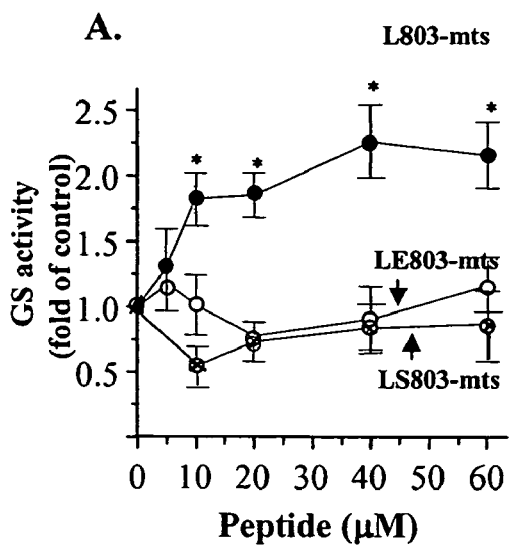
FIGS. 5a-b present comparative plots and a bar graph, respectively, demonstrating the GSK-3 inhibition activity of L803-mts in intact cells. HEK293 cells were treated with L803-mts or the control peptides LE803-mts or LS803-mts for 2.5 hours at indicated concentrations and lysate supernatants were assayed for glycogen synthase activity thereafter. The activity of glycogen synthase in cells treated With vehicle only (0.1% DMSO) was normalized to 1 unit and the values for glycogen synthase activity observed in cells treated with L803-mts (filled circles) and its respective controls LE803-mts (open circles) and LS803-mts (x-filled circles) are presented in FIG. 5a as fold stimulation over the cells treated with vehicle only. Data are mean of three independent experiments±SEM, where each point was assayed in duplicate. * indicates a value significantly greater than the values obtained in control peptides-treated cells.
Figure 5B:
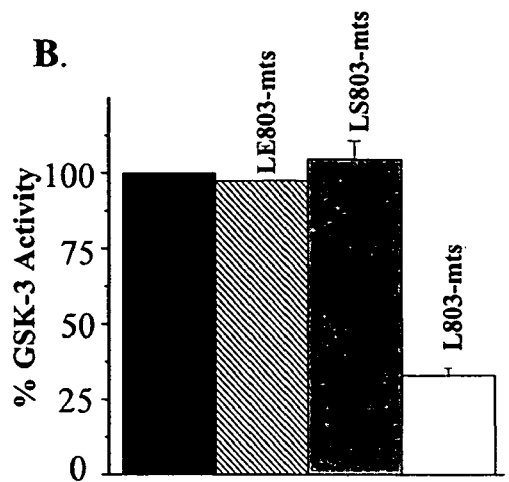

The results obtained in these studies are presented in FIGS. 5a and 5b, indicating that L803-mts increased glycogen synthase activity by 2.5-fold as compared with cells treated with either LE803-mts or LS803-mts. These results further demonstrate that L803-mts inhibit endogenous GSK-3 at relatively low concentrations (10-40 µM).

Figure 6A:
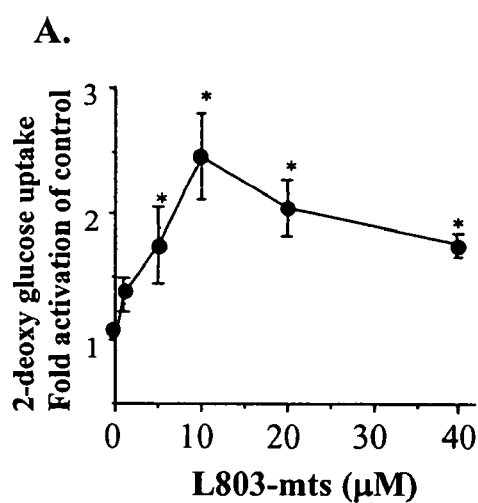
FIGS. 6a-b present plots demonstrating the effect of L803-mts on glucose uptake in the absence (FIG. 6a) and presence (FIG. 6b) of insulin. Adipocytes were isolated from mouse epididymal fat tissue and incubated with L803-mts for 75 minutes. Glucose uptake into cells was assayed with [$^3$H]2-deoxyglucose. The relative [$^3$H]2-deoxyglucose incorporation observed in adipocytes treated with the control peptide LE803-mts was normalized to 1 unit and the values obtained for [$^3$H]2-deoxyglucose in adipocytes treated with LE803-mts are presented in FIG. 6a as fold activation over cells treated with the peptide control, and are the mean of five independent experiments±SEM, where each point was assayed in triplicate. * indicate that the obtained value is significantly greater than control. In another experiment, adipocytes were treated with or without L803-mts at indicated concentrations for 30 minutes and insulin (5 nM) was added thereafter for another hour. Glucose uptake into cells was assayed with [$^3$H] 2-deoxyglucose. The results are presented in FIG. 6b as fold activation of glucose uptake in cells treated with L803-mts over cells treated with insulin (normalized as 1 unit), and are an average of four experiments±SEM, where each point was assayed in triplicate. * indicates that the obtained value is significantly greater than cells treated with insulin only.

Glucose Uptake in Isolated Adipocytes:

The impact of the conjugates of the present invention on glucose uptake in isolated adipocytes was examined by incubating mouse adipocytes with L803-mts, LS803-mts or LE803-mts for one hour before measuring the uptake of [$^3$H]-2-deoxyglucose. As is shown in FIG. 6a, L803-mts increased the incorporation of 2-deoxyglucose by approximately 2.5-fold as compared with cells treated with LE803-mts or LS803-mts. This value is comparable to that attained by maximum stimulation by insulin (10 nM), which is 3-fold in these mouse adipocytes (data not shown).

Figure 6B:
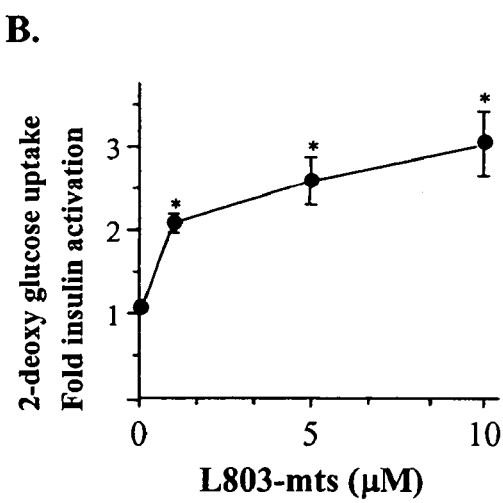

To determine whether the conjugate GSK-3 inhibitor of the present invention can work in concert with insulin, adipocytes were first treated with varied concentrations of L803-mts (1-10 µM) followed by the addition of a sub-optimal concentration of insulin (5 nM). As is shown in FIG. 6b, activation of glucose uptake in the L803-mts-treated cells was further increased in insulin-treated cells, indicating that L803-mts has an additive effect on insulin-induced glucose uptake.

Figure 7:
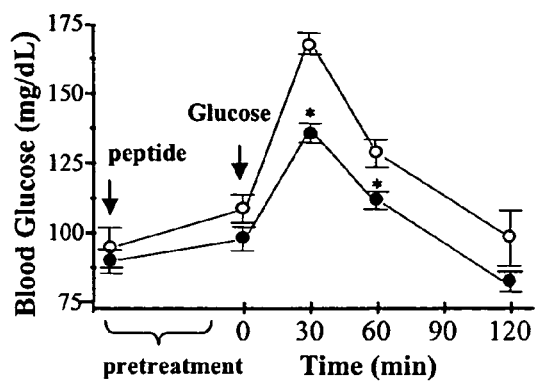
FIG. 7 presents comparative plots demonstrating the effect of L803-mts on glucose tolerance. Fasted mice were intraperitoneally injected with L803-mts or LE803-mts one hour prior to injection of glucose. Blood glucose (mg/dL) levels were measured at the indicated time points. The results are mean of 12 animals treated with L803-mts (filled circles) or 9 animals treated with control peptide LE803-mts (open circles)±SEM. * indicates that the obtained value is significantly less than animals treated with control peptide.

In Vivo Studies:

Glucose Tolerance Tests:

The function of L803-mts in vivo was tested by measuring the glucose tolerance after intraperitoneal administration of L803-mts in C57Bl/6J mice that had fasted overnight, as described hereinabove. The results, presented in FIG. 7, demonstrate that a better glucose tolerance was observed in fasted mice that were pretreated with the GSK-3 inhibitor L803-mts as compared with mice treated with the control peptide. As is shown in FIG. 7, treatment with L803-mts resulted in a 20% reduction in the blood glucose peak as well as in subsequent glucose levels 1 and 2 hours after glucose administration.

Figure 8A:
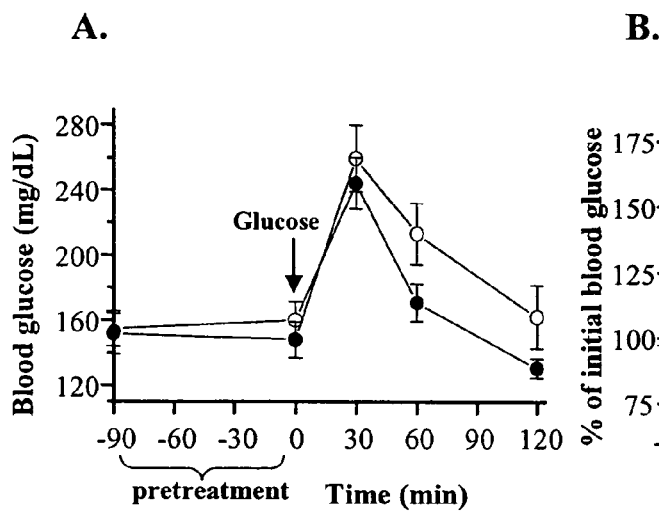
FIGS. 8a-b present comparative plots demonstrating the effect of L803-mts on glucose tolerance in diabetic mice. Following 6 hours fasting, HF mice were intraperitoneally injected with L803-mts (filled circles) or LE803-mts (open circles) 90 minutes prior to injection of glucose (1 gram/kg) and blood glucose levels were measured at the indicated time points (FIG. 8a). The results present the mean of 10 animals±SEM. * indicates that the obtained value is significantly less than animals treated with control peptide. The percent of the blood glucose levels measured at the time of glucose injection (time=0) in each group are presented in FIG. 8b.
Figure 8B:
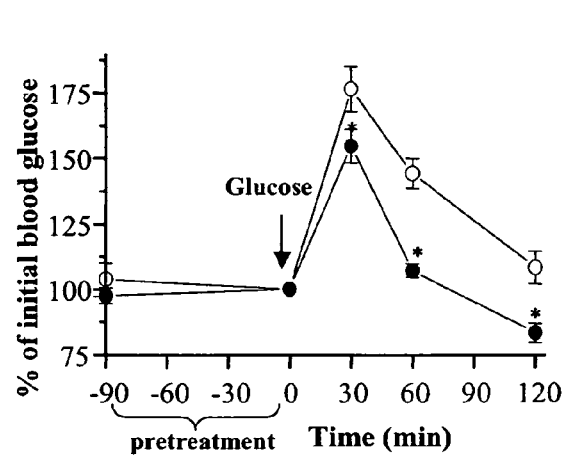

The effect of L803-mts on glucose tolerance in diabetic (HF) mice was next examined. As is shown in FIGS. 8a and 8b, HF mice that were pretreated with L803-mts exerted a significantly improved performance in glucose tolerance tests and blood glucose clearance as compared with the mice treated with the control peptide LE803-mts. These results are consistent with L803-mts capacity to enhance glucose uptake, and strongly support a role of GSK-3 in insulin resistance and type II diabetes.

Figure 9:
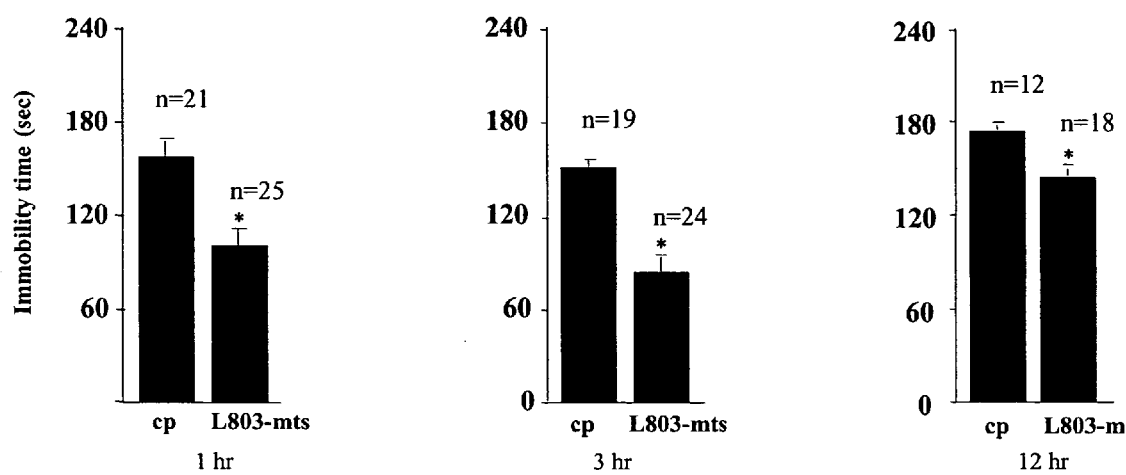
FIG. 9 presents a bar graph demonstrating the effect of L803-mts on animal behavior in the forced swimming test, as a mean of immobility±SE from indicated number of animals subjected to forced swimming test 1 hour, 3 hours and 12 hours post administration of L803-mts or scL803-mts (cp) as indicated. * p<0.05.

Forced Swimming Test Studies:

L803-mts was i.c.v. injected 1 hour, 3 hours or 12 hours before FST. The results are presented in FIG. 9, and show that pretreatment with L803-mts significantly shortened immobility time duration periods by 37%±3.7% (1 hour), 44%±5.7% (3 hours) and 16%±0.6% (12 hours), as compared with control-treated animals that became immobile after a brief duration of swimming (p<0.05 for all).

As the forced swimming test is a behavioral test widely used as an animal model for assessing antidepressant activity, these results demonstrate for the first time that in vivo inhibition of GSK-3 provokes anti-depressive-like activity, thus indicating that specific GSK-3 inhibitors can alter depressive behavior in an animal model, and may serve as a promising new class of antidepressants and/or mood stabilizers.

β-catenin in Hippocampus of L803-mts Treated Mice:

β-catenin, a known substrate of GSK-3, is a multifunctional protein (Miller and Moon, 1996; Peifer and Polakis, 2000) that was recently implicated in brain development and cognitive activity (Coyle-Rink et al., 2002). Phosphorylation of β-catenin by GSK-3 enhances its proteosomal degradation, and inhibition of GSK-3 leads to the accumulation of hypo-phosphorylated β-catenin in the cytoplasm (Aberle et al., 1997; Ikeda et al., 1998; Yost et al., 1996). Once stabilized, β-catenin translocates to the nucleus, where it associates with the transcription factors of the Lef/Tcf family to stimulate gene expression (Behrens et al., 1996).

Figure 10:
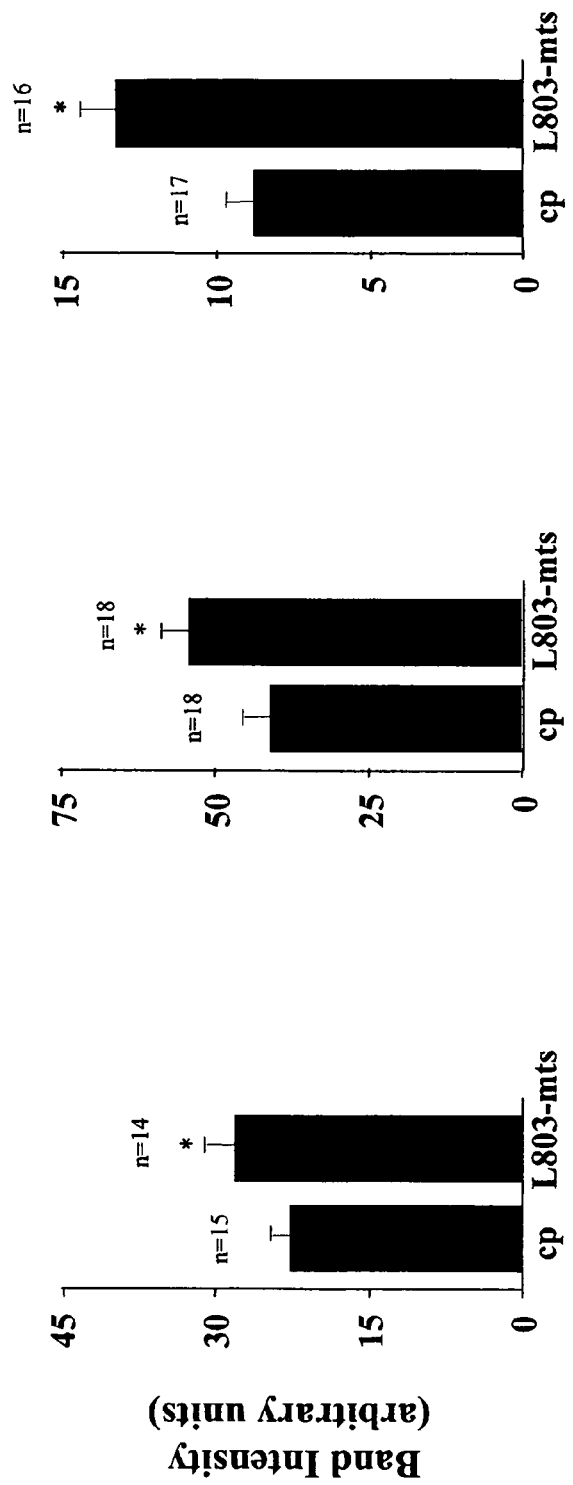
FIG. 10 presents bar graphs demonstrating the effect of L803-mts on β-catenin levels in mouse hippocampus 1 hour, 3 hours and 12 hours post administration of L803-mts or scL803-mts (cp). Hippocampal tissue extracts were prepared as described below and an equal amount of protein aliquots were subjected to gel electrophoresis and immunoblotted with antibody against β-catenin. The bar graphs present the densitometry analysis of β-catenin from indicated number of hippocampi and represent mean value±SE. * indicate p<0.05. At each time point, representative gels of β-catenin from cp-treated animals (lanes 1-4) or L803-mts-treated animals (lanes 5-8) are shown.

The effect of L803-mts on β-catenin levels in the mouse hippocampus was therefore tested. Hippocampal tissue extracts were analyzed by Western blot with a monoclonal anti-β-catenin antibody. As is shown in FIG. 10, L803-mts treatment increased the amount of β-catenin in hippocampus extracts in a time-dependent fashion. Increase of 20% and 30% in β-catenin levels were observed after 1 hour and 3 hours treatment with L803-mts, respectively (p<0.05 for both), whereby an increase of 50% was observed 12 hours post administration of L803-mts.

Up-regulation of β-catenin as a consequences of inactivation of GSK-3 has been implicated in numerous studies using various cultured cells treated with, Wnt, lithium or valproic acid (Chen et al., 1999; Ikeda et al., 1998; Sakanaka et al., 1998; Stambolic et al., 1996). In addition, GSK-3 expression was shown to inversely correlate with β-catenin levels in the brain (Hernandez et al., 2002; Lucas et al., 2001), and β-catenin signaling was further implicated in brain development and cognitive activity (Coyle-Rink et al., 2002).

However, the results of the FST and the hippocampus extracts studies indicate that up-regulation of β-catenin is associated with reduction in the immobility duration in response to treatment with L803-mts. It is noteworthy that increasing in β-catenin persisted 12 hours after L803-mts treatment, even though the effect of the inhibitor on immobility was reduced. Possibly, once accumulated in the nucleus, β-catenin is protected from proteosomal degradation and phosphorylation by GSK-3, that occurs mainly in the cytoplasm. These results may suggest that the up-regulation of β-catenin detected in these experiments is involved at least in part in the anti-depressive properties provoked by the GSK-3 inhibitor L803-mts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

Aberle H, Bauer A, Stappert J, Kispert A and Kemler R, "beta-catenin is a target for the ubiquitin-proteasome pathway", *EMBO J,* 16:3797-802 (1997).

American Diabetes Association, "Standards of Medical Care for Patients With Diabetes Mellitus", 21 Diabetes Care (1998).

Barber A J, Nakamura M, Wolpert E B, et al Insulin Rescues Retinal Neurons from Apoptosis by a Phosphatidylinositol 3-Kinase/Akt-mediated Mechanism That Reduces the Activation of Caspase-3. *J Biol Chem* 276:32814-821 (2001).

Beasley C, Cotter D, Khan N, Pollard C, Sheppard P, Varndell I, Lovestone S, Anderton B and Everall I, "Glycogen synthase kinase-3 beta immunoreactivity is reduced in the prefrontal cortex in schizophrenia" *Neurosci Lett* 302:117-20 (2001).

Behrense J, Von Kries J P, Kuhl M, Bruhn L, Weldlich D, Grosschedl R and Birchmeier W, "Functional interaction of beta-catenin with the transcription factor LEF-1" *Nature,* 382"638-42 (1996).

Berridge M J, Downes C P and Hanley M R, "Neural and developmental actions of lithium: a unifying hypothesis", *Cell* 59:411-419 (1989).

Bhat R V and Budd S L "GSK-3 beta signaling" casting a wide net in Alzheimer's disease" *Neurosignals* 11:251-61 (2002).

Bijur G N, De Sarno P, R S. J Glycogen synthase kinase-3 beta facilitates staurosporine- and heat shock-induced apoptosis. Protection by lithium *J Biol Chem* 275:7583-90 (2000).

Bradford M M, *Anal Biochem* 72:248-254 (1976).

Burke et al, "4'-O-[2-(2-fluoromalonyl)]-L-tyrosine: a phosphotyrosyl mimic for the preparation of signal transduction inhibitory peptides", *J Med Chem* 39(5):1021-1027 (1996a).

Burke et al, "Nonhydrolyzable phosphotyrosyl mimetics for the preparation of phosphatase-resistant SH2 domain inhibitors", *Biochemistry* 33(21):6490-6494 (1994a).

Burke et al, "Potent inhibition of insulin receptor dephosphorylation by a hexamer peptide containing the phosphotyrosyl mimetic F2Pmp", *Biochem Biophys Res Commun* 204 (1):129-133 (1994b).

Burke et al, "Small molecule interactions with protein-tyrosine phosphatase PTP1B and their use in inhibitor design", *Biochemistry* 35(50):15989-15996 (1996b).

Chen et al, "Why is phosphonodifluoromethyl phenylalanine a more potent inhibitory moiety than phosphonomethyl phenylalanine toward protein-tyrosine phosphatases?", *Biochem Biophys Res Commun* 216(3):976-984 (1995).

Chen G, Huang L D, Jiang Y M and Manji H K "The mood-stabilizeing agent. valproate inhibits the activity of glycogen synthase kinase-1" *J Neurochem* 72:1327-30 (1999).

Cheng K, Creacy S, Lamer J Insulin-like effect of lithium ion on isolated rat adipocytes stimulation of glycogenesis beyond glucose transport. *Mol. Cell. Biochem.* 56:177-182 (1983).

Cheng, K., Creacy, S. & Lamer, J. *Molecular & Cellular Biochemistry* 56, 183-9 (1983).

Cheng, K., Creacy, S. & Lamer, J. *Molecular & Cellular Biochemistry* 56, 177-82 (1983).

Chu et al, "Sequential phosphorylation by mitogen-activated protein kinase and glycogen synthase kinase 3 represses transcriptional activation by heat shock factor-1", *J Biol Chem* 271(48):30847-30857 (1996).

Coghlan, M. P., Culbert, A. A., Cross, D. A., Corcoran, S. L., Yates, J. W., Pearce, N. J., Rausch, O. L., Murphy, G. J., Carter, P. S., Roxbee Cox, L., Mills, D., Brown, M. J., Haigh, D., Ward, R. W., Smith, D. G., Murray, K. J., Reith, A. D. & Holder, J. C. *Chemistry & Biology* 7, 793-803 (2000).

Cohen, P. Muscle glycogen synthase, The enzymes, edited by Boyer. P, and Krebs, E. G. (Academic Press, Orlando, Fla.) (1986).

Coyle-Rink L, Del Valle L, Sweet T, Khalili K and Amini S, "development expression of Wnt signaling factors in mouse brain" *Cancer Biol Ther* 1:640-5 (2002).

Cross D. A., Culbert A. A., Chalmers K. A., Facci L., Skaper S. D., Reith, A. D. *J Neurochem* 77:94-102 (2001).

Cross et al, "Inhibition of glycogen synthase kinase-3 by insulin mediated by protein kinase B", *Nature* 378(6559): 785-78 (1995).

Cross, D. A., Alessi, D. R., Vandenheede, J. R., McDowell, H. E., Hundal, H. S. & Cohen, P. *Biochem. J.* 303, 21-26 (1994).

Crowder R J, R S. F Glycogen synthase kinase-3 beta activity is critical for neuronal death caused by inhibiting phosphatidylinositol 3-kinase or Akt but not for death caused by nerve growth factor withdrawal. *J Biol Chem* 275:34266-71 (2000).

Dajani et al., "Crystal structure of glycogen synthase kinase 3β: structural basis for phosphate-primed substrate specificity and auto inhibition", *Cell* 105:721-732 (2001).

Damiens, E., Baratte, B., Marie, D., Eisenbrand, G. & Meijer, L. *Oncogene* 20, 3786-97 (2001).

Damsbo, P., Vaag, A., Hother-Nielsen, O. & Beck-Nielsen, H. *Diabetologia* 34, 239-45 (1991).

Davies, S. P., Reddy, H., Caivano, M. & Cohen, P. *Biochemical Journal* 351, 95-105 (2000).

Devlin, *Textbook of Biochemistry with Clinical Correlations*, 4th Ed. (Wiley-Liss, Inc., 1997).

Dugas et al, *Bioorganic Chemistry* (Springer-Verlag, New York, 1981), pp 54-92.

Eldar-Finkelman et al, "Expression and characterization of glycogen synthase kinase-3 mutants and their effect on glycogen synthase activity in intact cells", *Proc Natl Acad Sci USA* 93(19): 10228-10233 (1996).

Eldar-Finkelman et al, "Increased glycogen synthase kinase-3 activity in diabetes- and obesity-prone C57BL/6J mice", *Diabetes* 48(8):1662-1666 (1999).

Eldar-Finkelman et al, "Phosphorylation of insulin receptor substrate 1 by glycogen synthase kinase 3 impairs insulin action", *Proc Natl Acad Sci USA* 94(18):9660-9664 (1997).

Eldar-Finkelman, H. & Krebs, E. G. *Proc. Natl. Acad. Sci.* 94, 9660-9664 (1997).

Eldar-Finkelman, H. *Trend. Mol. Med.* 8, 126-132 (2002).

Eldar-Finkelman, H., Agrast, G. M., Foord, O., Fischer, E. H. & Krebs, E. G. *Proc. Natl. Acad. Sci. USA* 93, 10228-10233 (1996).

Eldar-Finkelman, H., Schreyer, S. A., Shinohara, M. M., LeBoeuf, R. C. & Krebs, E. G. *Diabetes* 48, 1662-1666 (1999).

Emoto, M., Langille, S. E. & Czech, M. P. *J. Biol. Chem.* 276, 10677-82 (2001).

Fiol et al, "A secondary phosphorylation of CREB341 at Ser129 is required for the cAMP-mediated control of gene expression. A role for glycogen synthase kinase-3 in the control of gene expression", *J Biol Chem* 269(51):32187-32193 (1994).

Fiol et al, "Formation of protein kinase recognition sites by covalent modification of the substrate. Molecular mechanism for the synergistic action of casein kinase II and glycogen synthase kinase 3", *J Biol Chem* 262(29):14042-14048 (1987).

Fiol et al, "Ordered multisite protein phosphorylation. Analysis of glycogen synthase kinase 3 action using model peptide substrates", *J Biol Chem* 265(11):6061-6065(1990).

Fiol et al, "Phosphoserine as a recognition determinant for glycogen synthase kinase-3: phosphorylation of a synthetic peptide based on the G-component of protein phosphatase-1 *Arch Biochem Biophys* 267(2):797-802 (1988).

Fiol, C. J., Mahrenholz, A. M., Wang, Y., Roeske, R. W. & Roach, P. J. (1987) *J. Biol. Chem.* 262, 14042-8.

Fu et al, Design and synthesis of a pyridone-based phosphotyrosine mimetic", *Bioorg Med Chem Lett* 8(19):2813-2816 (1998).

Gao et al, "Inhibition of Grb2 SH2 domain binding by non-phosphate-containing ligands. 2. 4-(2-Malonyl)phenylalanine as a potent phosphotyrosyl mimetic", *J Med Chem* 43(5):911-920 (2000).

Gething et al, "Cell-surface expression of influenza haemagglutinin from a cloned DNA copy of the RNA gene *Nature* 293(5834):620-625 (1981).

Grimes C A and Jope R S "The multifunctional roles of glycogen synthase kinase 3 beta in cellular signaling" *Prog Neurobiolo* 65-391-426 (2001).

Groves et al, "Structural basis for inhibition of the protein tyrosine phosphatase 1B by phosphotyrosine peptide mimetics", *Biochemistry* 37(51):17773-17783 (1998).

Hallstrom et al, "Regulation of transcription factor Pdr1p function by an Hsp70 protein in *Saccharomyces cerevisiae*", *Mol Cell Biol* 18(3):1147-1155 (1998).

Hanger D P, Hughes K, Woodgett J R, Brion J P, Anderton B H Glycogen synthase kinase-3 induces Alzheimer's disease-like phosphorylation of tau: generation of paired helical filament epitopes and neuronal localisation of the kinase. *Neurosci. Lett.* 147:58-62 (1992).

Hawiger J, "Cellular import of functional peptides to block intracellular signaling *Curr Opin Immunol* 9(2):189-194 (1997).

Hawiger, J. *Curr. Opin. Immun.* 9, 189-194 (1997).

Hawiger, J. (*Curr. Opin. Chem. Biol.* 3, 89-94 1999).

He et al, Glycogen synthase kinase-3 and dorsoventral patterning in *Xenopus* embryos", *Nature* 374(6523):617-622 (1995).

Heinemann, L., Pfutzner, A. & Heise, T. *Curr. Pharm. Des.* 14, 1327-1351 (2001).

Herbst, J. J., Andrews, G. C., Contillo, L. G., Singleton, D. H., Genereux, P. E., Gibbs, E. M. & Lienhard, G. E. *J. Biolo. Chem.* 270, 26000-5 (1995).

Hernandez F, Borrell J, Guaza C, Avila J and Lucas J J "Spatila learning deficit in transgenic mice that conditionally over-express GSK-3 beta in the brain but do not form tau filaments" *J Neurohem* 83:1529-33 (2002).

Higashimoto et al, "Human p53 is phosphorylated on serines 6 and 9 in response to DNA damage-inducing agents", *J Biol Chem* 275(30):23199-23203 (2000).

Ikeda S, Kishida S, Yamamoto H. Murai H, Koyama S and Kikuchi A "Axin, a negative regulator of the Wnt signaling pathway, forms a complex with GSK-3 beta and beta-catenin and promotes GSK-3 beta-dependent phosphorylation of beta-catenin" *EMBO J* 17:1371-84 (1998).

Jope R S and Bijur G N "Mood stabilizers, glycogen synthase kinase-3 beta and cell survival" *Molecular Psychiatry* 7(1): S35-45 (2002).

Jung, T., Kamm, W., Breitenbach, A., Kaiserling, E., Xiao, J. X. & Kissel, T. *Euro. J. Pharma. Biopharma.* 50, 147-60 (2000).

Katagiri, H., Asano, T., Ishihara, H., Inukai, K., Shibasaki, Y., Kikuchi, M., Yazaki, Y. & Oka, Y. *J Biol Chem* 271, 16987-90 (1996).

Klein P S, Melton DA "A Molecular Mechanism for the Effect of Lithium on Development". *Proc. Natl. Acad. Sci. USA* 93:8455-8459 (1996).

Kole et al, "Protein-tyrosine phosphatase inhibition by a peptide containing the phosphotyrosyl mimetic, L-O-malonyltyrosine", *Biochem Biophys Res Commun* 209(3):817-822 (1995).

Kole et al, "Specific inhibition of insulin receptor dephosphorylation by a synthetic dodecapeptide containing sulfotyrosyl residues as phosphotyrosyl mimetic", *Indian J Biochem Biophys* 34(1-2):50-55 (1997).

Latimer et al, "Stimulation of MAP kinase by v-raf transformation of fibroblasts fails to induce hyperphosphorylation of transfected tau", *FEBS Lett* 365:42-46 (1995).

Lawrence, J. C., Guinovart, J. J. & Lamer, J. *J. Biol. Chem.* 252, 444-450 (1977).

Lovestone et al, *Curr Biol* 4:1077-1086 (1995).

Lucas J J, Hernandez F, Gomez-Ramos P, Moran M A, Hen R, J. A "Decreased nuclear beta-catenin, tahyperphosphorylation and neurodegeneration in GSK-3beta conditional transgenic mice". *EMBO J* 20:27-39 (2001).

Mandelkow E M, Drewes G, Biernat J, et al "Glycogen synthase kinase-3 and the Alzheimer-like state of microtubule-associated protein tau". *Febs Lett.* 314:315-21 (1992).

Mandelkow et al, "Tau as a marker for Alzheimer's disease", *Trends Biochem Sci.* 18(12):480-483 (1983).

Manji et al, "Lithium at 50: have the neuroprotective effects of this unique cation been overlooked?", *Biol Psychiatry* 46(7):929-940 (1999).

Manji H K and Lenox R H "Signaling: cellular insights into the pathophysiology of bipolar disorder" *Biol. Psych.* 48:518-30(2001).

Mauvais-Jarvis, F., Ueki, K., Fruman, D. A., Hirshman, M. F., Sakamoto, K., Goodyear, L. J., Iannacone, M., Accili, D., Cantley, L. C. & Kahn, C. R. *J. Clin. Invest.* 109, 141-9 (2002).

McKinsey et al, "Phosphorylation of the PEST domain of IkappaBbeta regulates the function of NF-kappaB/IkappaBbeta complexes", *J Biol Chem* 272(36):22377-22380 (1997).

Merrifield et al, *J Am Chem Soc* 85:2149 (1964).

Mikol et al, "The crystal structures of the SH2 domain of p56lck complexed with two phosphonopeptides suggest a gated peptide binding site", *J Mol Biol* 246(2):344-355 (1995).

Miller J R and Moon R T "Signal transduction through beta-catenin and specofocation of cell fate during embryogenesis" *Genes & development* 10:2527-39 (1996).

Morfini, G., Szebenyi, G., Elluru, R., Ratner, N. & Brady, S. T. *EMBO J.* 21, 281-93 (2002).

Morrison et al, *Organic Chemistry*, 6th Ed. (Prentice Hall, 1992).

Mulot et al, "Phosphorylation of tau by glycogen synthase kinase-3 beta in vitro produces species with similar electrophoretic and immunogenic properties to PHF-tau from Alzheimer's disease brain", *Biochem Soc Trans* 23(1):45S (1995).

Mulot et al, "PHF-tau from Alzheimer's brain comprises four species on SDS-PAGE which can be mimicked by in vitro phosphorylation of human brain tau by glycogen synthase kinase-3 beta", *FEBS Lett* 349(3):359-364 (1994).

Myers et al, "RS-1 activates phosphatidylinositol 3'-kinase by associating with src homology 2 domains of p85d", *Proc Natl Acad Sci USA* 89(21):10350-10354 (1992).

Nicolaou et al, "Design and synthesis of a peptidomimeticemploying β-D-glucose for scaffolding" in *Peptides*, Rivier and Marshall (eds) ESCOM (1990).

Nikoulina et al, "Potential role of glycogen synthase kinase-3 in skeletal muscle insulin resistance of type 2 diabetes", *Diabetes* 49(2):263-271 (2000).

Nikoulina et al, "Regulation of glycogen synthase activity in cultured skeletal muscle cells from subjects with type II diabetes: role of chronic hyperinsulinemia and hyperglycemia", *Diabetes* 46(6):1017-1024 (1997).

Nonaka et al., *Proc. Natl. Acad. Sci. USA*, 95:2642-2647 (1998).

Otaka et al, *Chem Commun* (12):1081-1082 (2000).

Otaka et al, *Tetrahedron Lett* 36(6):927-30 (1995).

Pap M, Cooper G "Role of glycogen synthase kinase-3 in the phosphatidylinositol 3-Kinase/Akt cell survival pathway". *J. Biol. Chem.* 273:19929-32 (1998).

Peifer M and Polakis P "Wnt signaling in oncogensis and embryogenesis—a look outside the nucleus" *Science* 287: 1606-9 (2000).

Phiel C J, Klein PS "Molecular targets of lithium action". *Annu Rev Pharmacol Toxicol* 41:789-813 (2001).

Porsolt R D, Le Pichon M and Jalfre M "Depression: a new animal model sensitive to antidepressant treatments" *Nature* 266:730-2 (1977).

Rich D H, in *Protease Inhibitors*, Barrett and Selveson (eds) Elsevier (1986).

Ricort, J. M., Tanti, J. F., Van Obberghen, E. & Le Marchand-Brustel, Y. *Eur. J. Biochem.* 239, 17-22 (1996).

Rojas, M., Yao, S. & Lin, Y. Z. *J. Biol. Chem.* 271, 27456-61 (1996).

Roller et al, "Potent inhibition of protein-tyrosine phosphatase-1B using the phosphotyrosyl mimetic fluoro-O-malonyl tyrosine (FOMT)", *Bioorg Med Chem Lett* 8(16):2149-2150 (1998).

Rubinfeld et al, "Binding of GSK3beta to the APC-beta-catenin complex and regulation of complex assembly", *Science* 272(5264):1023-1026 (1996).

Sakanaka C, Weiss J B and Williams L T "Bridging of beta-catenin and glycogen synthase kinase-3 beta by axin and inhibition of beta-catenin mediated transcription" *Proc Natl Acad Sci USA* 95:3020-3 (1998).

Sakaue, H., Ogawa, W., Takata M, Kuroda S, Kotani K, Matsumoto M, Sakaue M, Nishio S, Ueno, H. & Kasuga, M. K. *Mol. Endocrin.* 10, 1552-62 (1997)

Sambrook et al, *Molecular Cloning: A Laboratory Manual*, 2nd Ed. (Cold Spring Harbor Press, 1989).

Schiller et al, *Int J Pent Prot Res* 25:171 (1985).

Senel, S., Kremer, M., Nagy, K. & Squier, C. *Curr. Pharm. Biotechnol.* 2, 175-186 (2001).

Shapiro et al, "Combined Fmoc-Alloc strategy for a general SPPS of phosphoserine peptides; preparation of phosphorylation-dependent tau antisera", *Bioorg Med Chem* 5(1): 147-56 (1997).

Sherman et a, *J Am Chem Soc* 112:433 (1990).

Shulman et al, "Quantitation of muscle glycogen synthesis in normal subjects and subjects with non-insulin-dependent diabetes by 13C nuclear magnetic resonance spectroscopy", *N Engl J Med* 322(4):223-228 (1990).

Stambolic V, Ruel L, Woodgett J R "Lithium inhibits glycogen synthase kinase-3 activity and mimics wingless signalling in intact cells". *Curr. Biol.* 6:1664-1668 (1996).

Surwit, R. S., Kuhn, C. M., Cochrane, C., McCubbin, J. A. & Feinglos, M. N. *Diabetes* 37, 1163-67 (1988).

Ter Haar et al., "Structure of GSK-3 beta reveals a primed phosphorylation mechanism", *Nat. Struct. Biol.* 8(7):593-6 (2001).

Thomas, J. A., Schiender, K. K. & Lamer, J. *Anal. Biochem.* 25, 486-499 (1968).

Thomas, *J. Am. Geriatr. Soc.,* 43:1279-89 (1995).

Thorsett et al, "Dipeptide mimics. Conformationally restricted inhibitors of angiotensin-converting enzyme", *Biochem Biophys Res Commun* 111(1):166-171 (1983).

Tong N, Sanchez J F, Maggirwar S B, et al "Activation of glycogen synthase kinase 3 beta (GSK-3beta) by platelet activating factor mediates migration and cell death in cerebellar granule neurons". *Eur J Neurosci* 13:1913-22 (2001).

Ueki, K., Yballe, C. M., Brachmann, S. M., Vicent, D., Watt, J. M., Kahn, C. R. & Cantley, L. C. *Proc. Natl. Acad. Sci. USA* 99, 419-24 (2002).

Veber et al, "Conformationally restricted bicyclic analogs of somatostatin", *Proc Natl Acad Sci USA* 75(6):2636-2640 (1978).

Wang, Y. & Roach, P. J. *J. Biol. Chem.* 268, 23876-23880 (1993).

Welsh et al, "Glycogen synthase kinase-3 is rapidly inactivated in response to insulin and phosphorylates eukaryotic initiation factor eIF-2B", *Biochem J* 294(Pt 3):625-629 (1993).

Wiemann et al, *Tetrahedron* 56:1331-1337 (2000).

Woodgett, J. R. & Cohen, P. *Biochim. Biophys. Acta.* 788, 339-47 (1984).

Woodgett, J. R. *Sci. STKE* 100, RE12 (2001).

Ye et al, "L-O-(2-malonyl)tyrosine: a new phosphotyrosyl mimetic for the preparation of Src homology 2 domain inhibitory peptides", *J Med Chem* 38(21):4270-4275 (1995).

Yost C, Torres M, Miller J, Huang E, Kimelman D and Moon R "The axis-inducing activity, stability and subcellular disribution of beta-catenin is regulated in *Xenopus* embryos by glycogen synthase kinase 3 "*Genes* 10:1443-1454 (1996).

Zasloff, M. *Nature* 415, 389-95 (2002).

Zhang, W., Depaoli-Roach, A. A. & Roach, P. J. *Arch. Biochem. Biophys.* 304, 219-25 (1993).

Zhang, Z. H., Johnson, J. A., Chen, L., El-Sherif, N., Mochly-Rosen, D. & Boutjdir, M. *Circ. Res.* 80, 720-9 (1997).

What is claimed is:

1. A conjugate having the amino acid sequence set forth in SEQ ID NO:16.

2. A pharmaceutical composition comprising, as an active ingredient, the conjugate of claim 1, and a pharmaceutically acceptable carrier.

3. The pharmaceutical composition of claim 2, packaged in a packaging material and identified in print, on or in said packaging material, for use in the treatment of a biological condition associated with GSK-3 activity.

4. The pharmaceutical composition of claim 3, wherein said biological condition is selected from the group consisting of obesity, non-insulin dependent diabetes mellitus, an insulin-dependent condition, an affective disorder, a neurodegenerative disease or disorder and a psychotic disease or disorder.

5. A pharmaceutical composition comprising, as an active ingredient, a conjugate which comprises:

(a) a polypeptide having the amino acid sequence:

$$[Y_n \cdots Y_1] Z X_1 X_2 X_3 S(p) [W_1 \cdots W_m]$$

wherein m equals 1 or 2;

n is an integer from 3 to 7, such that said polypeptide consists of 10 to 13 amino acid residues;

S(p) is a phosphorylated serine residue or a phosphorylated threonine residue;

Z is any amino acid residue excepting serine residue or threonine residue; and $X_1, X_2, X_3, Y_1$-Yn and $W_1$-Wm are each independently any amino acid residue; and (b) at least one hydrophobic moiety being attached to said polypeptide, said at least one hydrophobic moiety comprising a fatty acid, the conjugate being capable of inhibiting an activity of glycogen synthase kinase-3 (GSK-3), wherein the hydrophobic moiety provides the conjugate with better (i) membrane permeability and/or (ii) interaction with the hydrophobic patch of the GSK-3, and a pharmaceutically acceptable carrier, the composition further comprising at least one additional active ingredient that is capable of altering an activity of GSK-3.

6. The pharmaceutical composition of claim 5, wherein said additional active ingredient is insulin.

7. The pharmaceutical composition of claim 5, wherein said additional active ingredient is capable of inhibiting an activity of GSK-3.

8. The pharmaceutical composition of claim 5, wherein said additional active ingredient is capable of downregulating an expression of GSK-3.

9. A pharmaceutical composition comprising, as an active ingredient, a conjugate which comprises:

(a) a polypeptide having the amino acid sequence:

$$[Y_n \cdots Y_1] Z X_1 X_2 X_3 S(p) [W_1 \cdots W_m]$$

wherein, m equals 1 or 2;

n is an integer from 3 to 7, such that said polypeptide consists of 10 to 13 amino acid residues;

S(p) is a phosphorylated serine residue or a phosphorylated threonine residue;

Z is any amino acid residue excepting serine residue or threonine residue; and $X_1, X_2, X_3, Y_1$-Yn and $W_1$-Wm are each independently any amino acid residue; and (b) at least one hydrophobic moiety being attached to said polypeptide, said at least one hydrophobic moiety being a hydrophobic peptide sequence which consists of at least five consecutive amino acid residues selected from the group consisting of an alanine residue, a cysteine residue, a glycine residue, an isoleucine residue, a leucine residue, a valine residue, a phenylalanine residue, a tyrosine residue, a methionine residue, a proline residue and a tryptophan residue.

the conjugate being capable of inhibiting an activity of glycogen synthase kinase-3 (GSK-3), wherein the hydrophobic moiety provides the conjugate with better (i) membrane permeability and/or (ii) interaction with the hydrophobic patch of the GSK-3, and a pharmaceutically acceptable carrier, the composition further comprising at least one additional active ingredient that is capable of altering an activity of GSK-3.

* * * * *

```
                        SEQUENCE LISTING

<160> NUMBER OF SEQ ID NOS: 19

<210> SEQ ID NO 1
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: PHOSPHORYLATION

<400> SEQUENCE: 1

Lys Arg Arg Glu Ile Leu Ser Arg Arg Pro Ser Tyr Arg
1               5                   10

<210> SEQ ID NO 2
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: PHOSPHORYLATION

<400> SEQUENCE: 2

Ile Leu Ser Arg Arg Pro Ser Tyr Arg
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic peptide

<400> SEQUENCE: 3

Ile Leu Ser Arg Pro Pro Glu Tyr Arg
1               5

<210> SEQ ID NO 4
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: PHOSPHORYLATION

<400> SEQUENCE: 4
```

Ile Leu Ser Arg Pro Pro Tyr Tyr Arg
1               5

<210> SEQ ID NO 5
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: PHOSPHORYLATION

<400> SEQUENCE: 5

Lys Arg Arg Glu Ile Leu Ala Arg Arg Pro Ser Tyr Arg
1               5                   10

<210> SEQ ID NO 6
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: PHOSPHORYLATION

<400> SEQUENCE: 6

Ile Leu Ala Arg Arg Pro Ser Tyr Arg
1               5

<210> SEQ ID NO 7
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: PHOSPHORYLATION

<400> SEQUENCE: 7

Lys Glu Glu Pro Pro Ser Pro Pro Gln Ser Pro
1               5                   10

<210> SEQ ID NO 8
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: PHOSPHORYLATION

<400> SEQUENCE: 8

Lys Glu Glu Pro Pro Ala Pro Pro Gln Ser Pro
1               5                   10

<210> SEQ ID NO 9
<211> LENGTH: 11
<212> TYPE: PRT
<213> ORGANISM: Artificial sequence
<220> FEATURE:
<223> OTHER INFORMATION: Synthetic peptide

```
<220> FEATURE:
<221> NAME/KEY: MOD_RES
<222> LOCATION: (10)..(10)
<223> OTHER INFORMATION: PHOSPHORYLATION

<400> SEQUENCE: 9

Lys Glu Ala Pro Pro Ala Pro Pro Gln Ser Pro
1               5                   10

<210> SEQ ID NO 10
<211> LENGTH: 11
<212> TYPE: PRT
<213> ORGANISM: Artificial sequence
<220> FEATURE:
<223> OTHER INFORMATION: Synthetic peptide

<400> SEQUENCE: 10

Lys Glu Glu Pro Pro Ala Pro Pro Gln Ser Pro
1               5                   10

<210> SEQ ID NO 11
<211> LENGTH: 11
<212> TYPE: PRT
<213> ORGANISM: Artificial sequence
<220> FEATURE:
<223> OTHER INFORMATION: Synthetic peptide

<400> SEQUENCE: 11

Lys Glu Glu Pro Pro Ala Pro Pro Gln Glu Pro
1               5                   10

<210> SEQ ID NO 12
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: PHOSPHORYLATION

<400> SEQUENCE: 12

Pro Ala Pro Pro Gln Ser Pro
1               5

<210> SEQ ID NO 13
<211> LENGTH: 8
<212> TYPE: PRT
<213> ORGANISM: Artificial sequence
<220> FEATURE:
<223> OTHER INFORMATION: Synthetic peptide

<400> SEQUENCE: 13

Glu Pro Pro Ala Pro Arg Arg Glu
1               5

<210> SEQ ID NO 14
<211> LENGTH: 6
<212> TYPE: PRT
<213> ORGANISM: Artificial sequence
<220> FEATURE:
<223> OTHER INFORMATION: Synthetic peptide

<400> SEQUENCE: 14

Glu Pro Pro Ala Pro Arg
1               5
```

```
<210> SEQ ID NO 15
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (21)..(21)
<223> OTHER INFORMATION: PHOSPHORYLATION

<400> SEQUENCE: 15

Tyr Arg Arg Ala Ala Val Pro Pro Ser Pro Ser Leu Ser Arg His Ser
1               5                   10                  15

Ser Pro Ser Gln Ser Glu Asp Glu Glu Glu
            20                  25

<210> SEQ ID NO 16
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: N'-myristolated peptide
<220> FEATURE:
<221> NAME/KEY: MOD_RES
<222> LOCATION: (11)..(11)
<223> OTHER INFORMATION: PHOSPHORYLATION

<400> SEQUENCE: 16

Gly Lys Glu Ala Pro Pro Ala Pro Pro Gln Ser Pro
1               5                   10

<210> SEQ ID NO 17
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: N'-myristolated peptide

<400> SEQUENCE: 17

Gly Lys Glu Ala Pro Pro Ala Pro Pro Gln Ser Glu Pro
1               5                   10

<210> SEQ ID NO 18
<211> LENGTH: 12
<212> TYPE: PRT
<213> ORGANISM: Artificial sequence
<220> FEATURE:
<223> OTHER INFORMATION: Synthetic peptide

<400> SEQUENCE: 18

Gly Lys Glu Ala Pro Pro Ala Pro Pro Gln Ser Pro
1               5                   10

<210> SEQ ID NO 19
<211> LENGTH: 5
<212> TYPE: PRT
<213> ORGANISM: Artificial sequence
<220> FEATURE:
<223> OTHER INFORMATION: Inhibitory peptide minimal consesus sequence
<220> FEATURE:
<221> NAME/KEY: misc_feature
<222> LOCATION: (2)..(4)
```

-continued

```
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: PHOSPHORYLATION

<400> SEQUENCE: 19

Ser Xaa Xaa Xaa Ser
1               5
```